(12) United States Patent
Hwang et al.

(10) Patent No.: US 12,128,130 B2
(45) Date of Patent: Oct. 29, 2024

(54) INJECTABLE COMPOSITION FOR PREVENTING HAIR LOSS OR STIMULATING HAIR GROWTH

(71) Applicant: KERAMEDIX INC., Seoul (KR)

(72) Inventors: Yu-Shik Hwang, Seoul (KR); Il-Keun Kwon, Seoul (KR); So Yeon Kim, Seoul (KR); Se Young Van, Daejeon (KR)

(73) Assignee: KERAMEDIX INC., Seoul (KR)

( * ) Notice: Subject to any disclaimer, the term of this patent is extended or adjusted under 35 U.S.C. 154(b) by 244 days.

(21) Appl. No.: 17/352,506

(22) Filed: Jun. 21, 2021

(65) Prior Publication Data

US 2021/0346283 A1 Nov. 11, 2021

Related U.S. Application Data

(63) Continuation of application No. 16/481,827, filed as application No. PCT/KR2017/013759 on Nov. 29, 2017, now abandoned.

(30) Foreign Application Priority Data

Jan. 31, 2017 (KR) ........................ 10-2017-0014047
Oct. 30, 2017 (KR) ........................ 10-2017-0142726

(51) Int. Cl.

| | | |
|---|---|---|
| *A61K 38/01* | (2006.01) | |
| *A61K 8/65* | (2006.01) | |
| *A61K 9/00* | (2006.01) | |
| *A61K 9/08* | (2006.01) | |
| *A61K 38/17* | (2006.01) | |
| *A61K 47/10* | (2017.01) | |
| *A61P 17/14* | (2006.01) | |
| *C12P 21/06* | (2006.01) | |

(52) U.S. Cl.
CPC .............. *A61K 9/0019* (2013.01); *A61K 8/65* (2013.01); *A61K 38/01* (2013.01); *A61K 38/1748* (2013.01); *A61K 47/10* (2013.01); *A61P 17/14* (2018.01); *C12P 21/06* (2013.01); *C12Y 304/21064* (2013.01)

(58) Field of Classification Search
None
See application file for complete search history.

(56) References Cited

U.S. PATENT DOCUMENTS

| | | |
|---|---|---|
| 6,270,793 B1 | 8/2001 | Van Dyke |
| 8,197,865 B2 | 6/2012 | Glynn |
| 2008/0274165 A1 | 11/2008 | Van Dyke |
| 2009/0111750 A1 | 4/2009 | Kelly |
| 2015/0152153 A1* | 6/2015 | Yu ...................... C07K 14/4741 435/68.1 |

FOREIGN PATENT DOCUMENTS

| | | | |
|---|---|---|---|
| CH | 703390 B1 | 1/2012 | |
| CN | 1634568 A | 7/2005 | |
| CN | 104487588 A | 4/2015 | |
| DE | 19831043 A1 | 1/2000 | |
| DE | 102009001343 A1 * | 9/2010 | ............... A61K 8/34 |
| JP | 2006124341 A | 5/2018 | |
| KR | 20050023051 A | 3/2005 | |
| KR | 20090094709 A | 9/2009 | |
| KR | 100966902 B1 | 6/2010 | |
| KR | 20130081003 A | 7/2013 | |
| KR | 20140056990 A | 5/2014 | |
| KR | 101509608 B1 | 4/2015 | |
| KR | 20160086649 A | 7/2016 | |
| KR | 101706515 B1 | 2/2017 | |
| WO | 2006099309 A2 | 9/2006 | |
| WO | 2015187951 A1 | 12/2015 | |
| WO | WO-2018143552 A2 * | 8/2018 | ............. A61K 35/00 |

OTHER PUBLICATIONS

Katchalski-Katzir et al., J. Molec. Catalysis B: Enzymatic 10:157-176 (2000) (Year: 2000).*
English language machine translation of WO 2018/143552 A2, 14 pages (2018) (Year: 2018).*
"Prevent", The Cambridge Dictionary, available online at https://dictionary.cambridge.org/us/dictionary/english/prevent, 8 pages (accessed on May 18, 2023) (Year: 2023).*
American Academy of Dermatology Association, "Hair Loss Types: Alopecia Areata Overview," available online at www.aad.org/public/diseases/hair-loss/types/alopecia, 3 pages (accessed on May 18, 2023) (Year: 2023).*
AIAMS, "Alopecia Areata," available online at www.niams.nih.gov/health-topics/alopecia-areata, 5 pages (last reviewed 2021) (Year: 2021).*
IQWiG, "Hair loss in chemotherapy: Can chemotherapy-related hair loss be prevented?", NCBI Bookshelf, available online at www.ncbi.nlm.nih.gov/books/NBK547555/, 3 pages (2019) (Year: 2019).*
Sigma Aldrich, "Proteinase K from Tritirachium album", available online at https://www.sigmaaldrich.com/catalog/product/sigma/sre0047?lang=en&region=US, 4 pages (first available 2015) (Year: 2015).*
Dwevedi et al., "Enzyme Immobilization: A Breakthrough in Enzyme Technology and Boon to Enzyme Based Industries," in Protein Structure, ed. Haggerty, LM, Nova Science Publishers, Inc., p. 31-50 (2011) (Year: 2011).*
Espacenet, English language abstract for DE 102009001343 A1, 1 page (2009) (Year: 2009).*

(Continued)

*Primary Examiner* — Thea D'Ambrosio
(74) *Attorney, Agent, or Firm* — Harvest IP Law, LLP

(57) ABSTRACT

The present invention relates to an injectable pharmaceutical composition containing keratin for preventing hair loss or stimulating hair growth, wherein the composition is excellent in hair follicle generating and hair growth stimulating effects, and thus can be favorably used as a preventive and therapeutic agent for hair loss or a stimulating agent for hair growth.

11 Claims, 12 Drawing Sheets

Specification includes a Sequence Listing.

(56) References Cited

OTHER PUBLICATIONS

EP OA dated Jun. 27, 2022.
EP Office Action dated Feb. 4, 2022.
IL Office Action dated Dec. 9, 2021.
VN Office Action dated Jan. 24, 2022.
Process Pharmaceutics 2nd Edition, Long Xiaoying et al., pp. 369-370.
The Chinese OA dated Feb. 22, 2023.
New hair from healing wounds, Nature. May 17, 2007; 447(7142): 265-266, Cheng-Ming Chuong.
Regeneration of Hair Follicles from Experimental Wounds on the Rabbit Ear, J Plast Reconstr Surg 8: 207-210, 1974, Goran Hallmans et al.
M2 macrophages promote wound-induced hair neogenesis, Journal of Dermatological Science 91 (2018) 250-255, Akira Kasuya et al.
The 500 Dalton rule for the skin penetration of chemical compounds and drugs, Exp Dermatol 2000: 9: 165-169., Jan D. Bos et al.
Keratin-mediated hair growth and its underlying biological mechanism, Communications Biology | (2022) 5:1270, Seong Yeong An et al.
Keratin-mediated Hair Growth and its Underlying Biological Mechanism, Seong Yeong An et al., Supplemental Information for Communications Biology (2022).

\* cited by examiner

FIG. 8
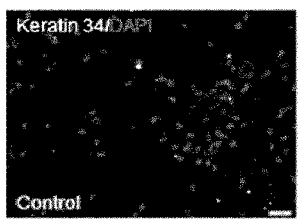
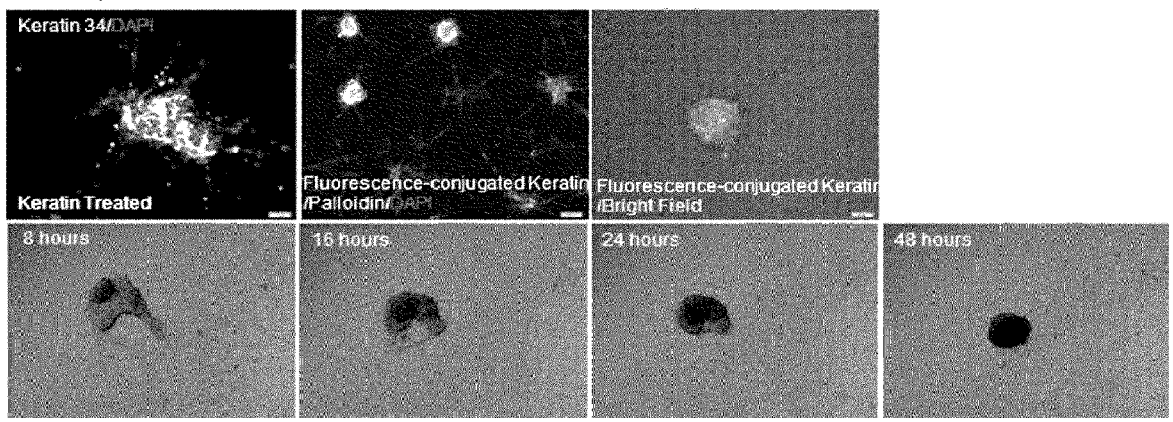

FIG. 9

RNA sequencing analysis

Upregulated Genes showing at least two fold Increase in Keratin Treated DP Cells

| Gene name | term |
|---|---|
| C-C motif chemokine ligand 20(CCL20) | cell-cell signaling |
| hepatocyte growth factor(HGF) | positive regulation of cell migration |
| proprotein convertase subtilisin/kexin type 1(PCSK1) | cell-cell signaling |
| C-X-C motif chemokine ligand 5(CXCL5) | cell-cell signaling |
| TNF alpha induced protein 6(TNFAIP6) | cell-cell signaling |
| integrin subunit beta 8(ITGB8) | extracellular matrix organization |
| C-C motif chemokine ligand 7(CCL7) | cell-cell signaling |
| nicotinamide phosphoribosyltransferase(NAMPT) | cell-cell signaling |
| tachykinin precursor 1(TAC1) | cell-cell signaling |
| fibroblast growth factor 13(FGF13) | cell-cell signaling |
| C-C motif chemokine ligand 11(CCL11) | positive regulation of cell migration |
| interleukin 11(IL11) | cell-cell signaling |
| matrix metallopeptidase 9(MMP9) | Cell migration |
| C-X-C motif chemokine ligand 6(CXCL6) | cell-cell signaling |
| gap junction protein beta 2(GJB2) | cell-cell signaling |
| chondroitin sulfate N-acetylgalactosaminyltransferase 1(CSGALNACT1) | extracellular matrix organization |
| solute carrier family 7 member 11(SLC7A11) | Cell migration |
| angiopoietin 1(ANGPT1) | Cell migration |
| neuromedin B(NMB) | cell-cell signaling |
| laminin subunit gamma 3(LAMC3) | extracellular matrix organization |
| cell migration inducing hyaluronan binding protein(CEMIP) | positive regulation of cell migration |
| integrin subunit beta 3(ITGB3) | extracellular matrix organization |
| integrin subunit alpha V(ITGAV) | extracellular matrix organization |
| EGF like domain multiple 6(EGFL6) | extracellular matrix organization |
| Wnt family member 5A(WNT5A) | positive regulation of cell migration |
| neuropilin 2(NRP2) | positive regulation of cell migration |
| platelet derived growth factor D(PDGFD) | positive regulation of cell migration |
| integrin subunit alpha 2(ITGA2) | extracellular matrix organization |
| collagen type IV alpha 2 chain(COL4A2) | extracellular matrix organization |
| SAM and SH3 domain containing 1(SASH1) | positive regulation of cell migration |
| intercellular adhesion molecule 1(ICAM1) | extracellular matrix organization |
| copine 3(CPNE3) | positive regulation of cell migration |
| neuropilin 1(NRP1) | cell-cell signaling |
| endoplasmic reticulum oxidoreductase 1 beta(ERO1B) | extracellular matrix organization |
| integrin subunit alpha 8(ITGA8) | extracellular matrix organization |
| E74 like ETS transcription factor 3(ELF3) | extracellular matrix organization |
| matrix metallopeptidase 1(MMP1) | Cell migration |
| laeverin(LVRN) | cell-cell signaling |
| olfactomedin like 2A(OLFML2A) | extracellular matrix organization |
| integrin subunit alpha 4(ITGA4) | extracellular matrix organization |
| lumican(LUM) | extracellular matrix organization |
| collagen type IV alpha 1 chain(COL4A1) | extracellular matrix organization |
| C-C motif chemokine ligand 8(CCL8) | cell-cell signaling |
| WNT1 inducible signaling pathway protein 1(WISP1) | cell-cell signaling |
| semaphorin 6D(SEMA6D) | positive regulation of cell migration |
| collagen type IV alpha 4 chain(COL4A4) | extracellular matrix organization |
| ASH1 like histone lysine methyltransferase(ASH1L) | cell-cell signaling |
| semaphorin 5A(SEMA5A) | cell-cell signaling |
| sphingosine-1-phosphate receptor 1(S1PR1) | positive regulation of cell migration |
| fibroblast growth factor 2(FGF2) | extracellular matrix organization |
| vascular endothelial growth factor A(VEGFA) | positive regulation of cell migration |
| laminin subunit alpha 1(LAMA1) | extracellular matrix organization |
| ABI family member 3 binding protein(ABI3BP) | extracellular matrix organization |
| platelet derived growth factor receptor alpha(PDGFRA) | positive regulation of cell migration |
| nidogen 1(NID1) | extracellular matrix organization |
| ATPase copper transporting alpha(ATP7A) | extracellular matrix organization |
| nidogen 2(NID2) | extracellular matrix organization |
| insulin like growth factor 1(IGF1) | positive regulation of cell migration |
| neurofibromin 1(NF1) | extracellular matrix organization |
| transforming growth factor beta receptor 1(TGFBR1) | positive regulation of cell migration |
| TNF receptor superfamily member 11b(TNFRSF11B) | extracellular matrix organization |
| ADAM metallopeptidase domain 17(ADAM17) | positive regulation of cell migration |
| nephrocystin 3(NPHP3) | extracellular matrix organization |
| thrombospondin 1(THBS1) | extracellular matrix organization |
| integrin subunit beta 2(ITGB2) | extracellular matrix organization |

Downregulated Genes showing at least two fold decrease in Keratin Treated DP Cells

| Gene name | term |
|---|---|
| tubulin alpha 1b(TUBA1B) | cell division |
| cyclin B2(CCNB2) | regulation of cell cycle |
| tubulin alpha 1a(TUBA1A) | G1/M transition of mitotic cell cycle |
| TPX2, microtubule nucleation factor(TPX2) | mitotic nuclear division |
| inhibitor of DNA binding 3, HLH protein(ID3) | regulation of cell cycle |
| cyclin B1(CCNB1) | regulation of cell cycle |
| protein kinase, membrane associated tyrosine/threonine 1(PKMYT1) | regulation of cell cycle |
| forkhead box M1(FOXM1) | regulation of cell cycle |
| cell division cycle associated 3(CDCA3) | mitotic nuclear division |
| ubiquitin conjugating enzyme E2 C(UBE2C) | cell division |
| eukaryotic translation initiation factor 4E binding protein 1(EIF4EBP1) | positive regulation of mitotic cell cycle |
| aurora kinase B(AURKB) | mitotic nuclear division |
| SPC24, NDC80 kinetochore complex component(SPC24) | mitotic nuclear division |
| pituitary tumor-transforming 1(PTTG1) | mitotic nuclear division |
| asparagine synthetase (glutamine-hydrolyzing)(ASNS) | positive regulation of mitotic cell cycle |
| baculoviral IAP repeat containing 5(BIRC5) | mitotic nuclear division |
| polo like kinase 1(PLK1) | regulation of cell cycle |
| cell division cycle 20(CDC20) | mitotic nuclear division |
| growth arrest and DNA damage inducible beta(GADD45B) | regulation of cell cycle |
| TMF1-regulated nuclear protein 1(TRNP1) | regulation of cell cycle |
| tubulin beta 3 class III(TUBB3) | mitotic nuclear division |
| MX dynamin like GTPase 2(MX2) | regulation of cell cycle |

FIG. 10
Control
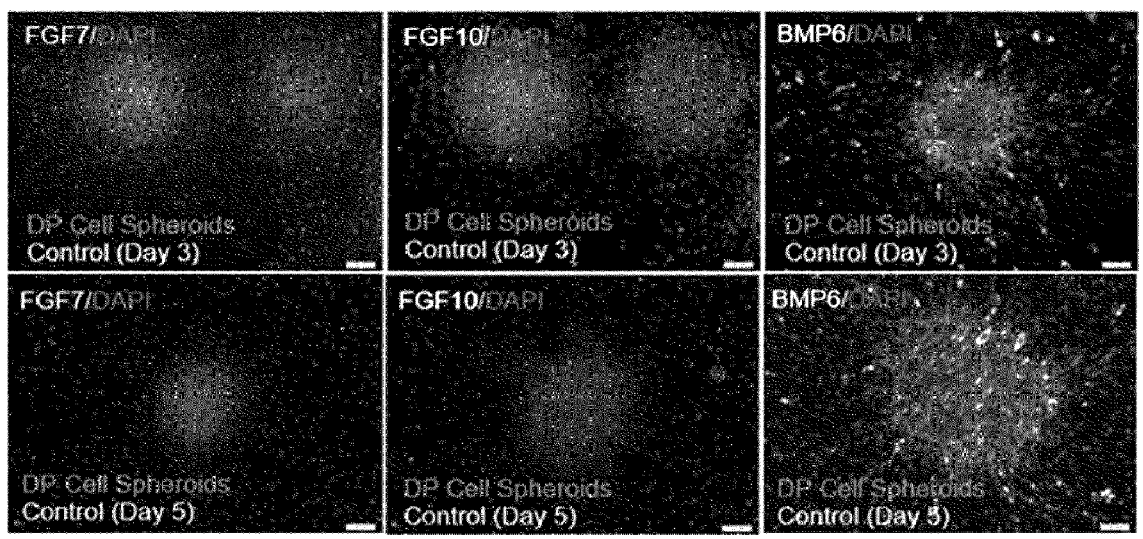
Example 1
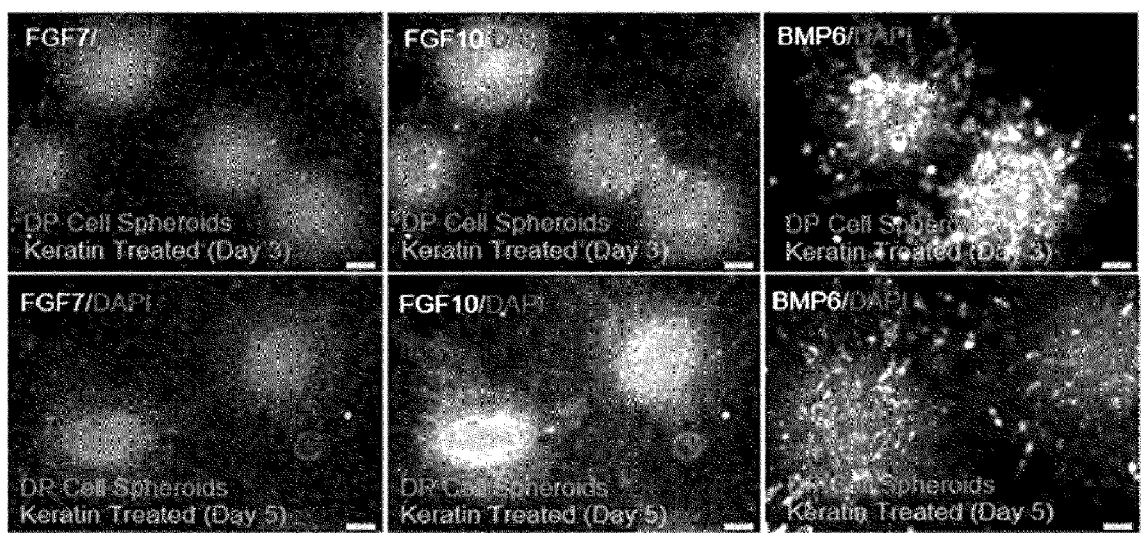

FIG. 14
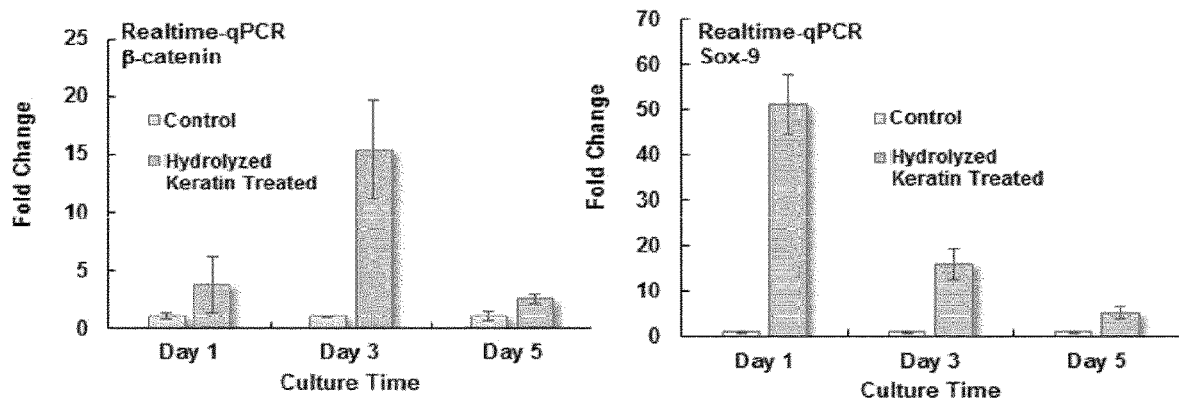
FIG. 15
Western Blot
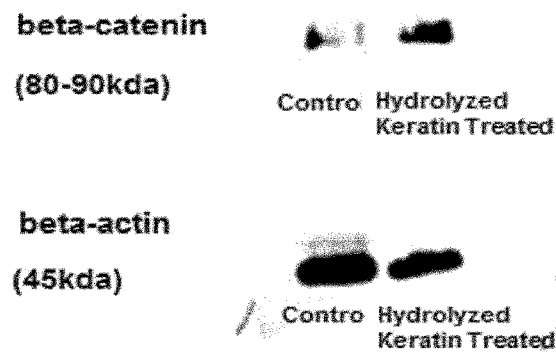
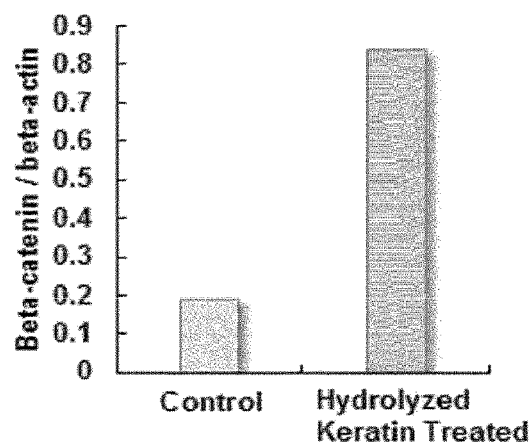

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: beta-catenin primerF

<400> SEQUENCE: 1
tgcagttcgc cttcactatg                    20

<210> SEQ ID NO 2
<211> LENGTH: 20
<212> TYPE: DNA
<213> ORGANISM: Artificial Sequence
<220> FEATURE:
<223> OTHER INFORMATION: beta-catenin primerR

<400> SEQUENCE: 2
ctgcacaaac aatggaatgg                    20

<210> SEQ ID NO 3

```
<211> LENGTH: 19
<212> TYPE: DNA
<213> ORGANISM: Artificial Sequence
<220> FEATURE:
<223> OTHER INFORMATION: KRT5 primerF

<400> SEQUENCE: 3
accagtaccc gcatctgca                                                    19

<210> SEQ ID NO 4
<211> LENGTH: 18
<212> TYPE: DNA
<213> ORGANISM: Artificial Sequence
<220> FEATURE:
<223> OTHER INFORMATION: KRT5 primerR

<400> SEQUENCE: 4
tgttccgtgg cctcttcg                                                     18

<210> SEQ ID NO 5
<211> LENGTH: 20
<212> TYPE: DNA
<213> ORGANISM: Artificial Sequence
<220> FEATURE:
<223> OTHER INFORMATION: MSX2 primerF

<400> SEQUENCE: 5
ccgccaagac atatgagccc                                                   20

<210> SEQ ID NO 6
<211> LENGTH: 20
<212> TYPE: DNA
<213> ORGANISM: Artificial Sequence
<220> FEATURE:
<223> OTHER INFORMATION: MSX2 primerR

<400> SEQUENCE: 6
acctgggtct ctgtgaggtt                                                   20

<210> SEQ ID NO 7
<211> LENGTH: 20
<212> TYPE: DNA
<213> ORGANISM: Artificial Sequence
<220> FEATURE:
<223> OTHER INFORMATION: ITGA6 primerF

<400> SEQUENCE: 7
agctgtgctt gctctacctg                                                   20

<210> SEQ ID NO 8
<211> LENGTH: 20
<212> TYPE: DNA
<213> ORGANISM: Artificial Sequence
<220> FEATURE:
<223> OTHER INFORMATION: ITGA6 primerR

<400> SEQUENCE: 8
ccggggtctc catatttccg                                                   20

<210> SEQ ID NO 9
<211> LENGTH: 20
<212> TYPE: DNA
<213> ORGANISM: Artificial Sequence
<220> FEATURE:
<223> OTHER INFORMATION: FOXN1 primerF

<400> SEQUENCE: 9
```

```
agtggtgctg ggatgttctg                                                20
```

<210> SEQ ID NO 10
<211> LENGTH: 20
<212> TYPE: DNA
<213> ORGANISM: Artificial Sequence
<220> FEATURE:
<223> OTHER INFORMATION: FOXN1 primerR

<400> SEQUENCE: 10

```
atagtgtgag gagcccaggt                                                20
```

<210> SEQ ID NO 11
<211> LENGTH: 20
<212> TYPE: DNA
<213> ORGANISM: Artificial Sequence
<220> FEATURE:
<223> OTHER INFORMATION: CD10 primerF

<400> SEQUENCE: 11

```
ctttagtgcc cagcagtcca                                                20
```

<210> SEQ ID NO 12
<211> LENGTH: 20
<212> TYPE: DNA
<213> ORGANISM: Artificial Sequence
<220> FEATURE:
<223> OTHER INFORMATION: CD10 primerR

<400> SEQUENCE: 12

```
gagtccacca gtcaacgagg                                                20
```

<210> SEQ ID NO 13
<211> LENGTH: 20
<212> TYPE: DNA
<213> ORGANISM: Artificial Sequence
<220> FEATURE:
<223> OTHER INFORMATION: beta-actin primerF

<400> SEQUENCE: 13

```
gtcaggcagc tcgtagctct                                                20
```

<210> SEQ ID NO 14
<211> LENGTH: 20
<212> TYPE: DNA
<213> ORGANISM: Artificial Sequence
<220> FEATURE:
<223> OTHER INFORMATION: beta-actin primerR

<400> SEQUENCE: 14

```
tcgtgcgtga cattaaggag                                                20
```

<210> SEQ ID NO 15
<211> LENGTH: 19
<212> TYPE: DNA
<213> ORGANISM: Artificial Sequence
<220> FEATURE:
<223> OTHER INFORMATION: Sox-9 primerF

<400> SEQUENCE: 15

```
accagtaccc gcatctgca                                                 19
```

<210> SEQ ID NO 16
<211> LENGTH: 18
<212> TYPE: DNA

```
<213> ORGANISM: Artificial Sequence
<220> FEATURE:
<223> OTHER INFORMATION: Sox-9 primerR

<400> SEQUENCE: 16
tgttccgtgg cctcttcg                                              18
```

INJECTABLE COMPOSITION FOR PREVENTING HAIR LOSS OR STIMULATING HAIR GROWTH

This is a continuation application of U.S. application Ser. No. 16/481,827 filed Jul. 29, 2019 which is a continuation application of International Patent Application No. PCT/KR2017/013759, filed Nov. 29, 2017, which claims the benefit of priority to Korean Patent Application No. 10-2017-0014047, filed Jan. 31, 2017 and No. 10-2017-0142726, filed Oct. 30, 2017 in the Korean Intellectual Property Office, the disclosures of which are incorporated herein by reference.

TECHNICAL FIELD

The present invention relates to an injectable composition containing keratin for preventing hair loss or stimulating hair growth.

BACKGROUND ART

Hair loss refers to a state in which there is no hair in a place where hair should be normally present, and genetic factors are known to be the main cause. Recently, due to environmental pollution, westernized eating habits such as instant foods, frequent perms and dyeing, and incorrect scalp cares as well as the increase of social stress, the population of hair loss is gradually increasing. However, the definite cause of hair loss has not yet been clarified. Recently, more and more people are suffering from alopecia, and the age group is lowering.

Even in the treatment of alopecia, there is still no clear effect, there are several taking prescriptions related to hair loss, such as Sineungyangjindan in Donguibogam, and there are methods of massaging sesame oil (sesame) in a hair loss area, applying a specific herbal medicine prescription by primary precipitate, and stimulating a specific acupoint, but it is known that there are many individual differences in the effect. In addition, there is still no report of a new drug substance that can be generally applied.

As a method for treating alopecia in the related art, there is a preparation using female hormone as a main material in relation to hormonal theory, but there is a report of occurrence of skin inflammation and adverse effects due to administration of hormone, and its use is being stopped at present. As a representative hair growth agent currently in use, there are minoxidil (6-amino-1,2-dihydro-1-hydroxy-2-imino-4-phenoxypyrimidine) in U.S. Pat. No. 3,382,247 and finasteride from Merck mentioned in U.S. Pat. No. 5,215,894, which have been first developed and used for stimulating blood circulation, have been known to patients using the hair growth agent to have a hair growth effect as side effects, and then have been approved by the US Food and Drug Administration (FDA) as a raw material for hair growth to be used as a hair growth treating agent.

However, the minoxidil has been reported to have a sticky feel and side effects that cause irritation to the skin, and the finasteride has been currently used as a preparation for oral administration, but adverse effects such as sexual dysfunction have been reported depending on its consumption, and there is a side effect to be taken steadily for hair loss.

Thus, it is necessary to develop a new therapeutic agent that can replace the existing hair growth agent and has an excellent effect of preventing hair loss and stimulating hair growth.

PRIOR ART DOCUMENTS

Patent Document (Patent Document 1) U.S. Pat. No. 3,382,247
(Patent Document 2) U.S. Pat. No. 5,215,894

DISCLOSURE

Technical Problem

In order to solve the problems, the present inventors discovered that keratin may stimulate hair growth or prevent hair loss while continuing a research about a new therapeutic agent that can replace existing hair growth agent. Furthermore the present inventors discovered that when the keratin was injected into the skin tissue, it was more effective in stimulating hair growth or preventing hair loss than when the keratin was applied to skin, and thus the inventors completed the present invention.

Therefore, an object of the present invention is to provide an injectable pharmaceutical composition containing keratin for preventing hair loss or stimulating hair growth.

Technical Solution

In order to achieve the object, according to one embodiment of the present invention, an injectable pharmaceutical composition is provided which contains keratin that prevents hair loss or stimulates hair growth.

In one embodiment of the present invention, the keratin may be hydrolyzed keratin or keratin linked to a water-soluble polymer.

The hydrolyzed keratin may have a molecular weight of 500 to 10,000 Daltons.

The water-soluble polymer may be selected at least one from the group consisting of hyaluronic acid, polyethylene glycol (PEG), alginic acid, pectin, carrageenan, chondroitin sulfate, dextran sulfate, chitosan, polylysine, collagen, gelatin, carboxymethyl chitin, fibrin, dextran, agarose, pullulan, polyacrylamide (PAAm), poly(N-isopropylacrylamide) (P(NIPAAm-co-AAc)), poly(N-isopropylacrylamide-co-ethylmethacrylate) (P(NIPAAm-co-EMA)), polyvinyl acetate/polyvinyl alcohol (PVAc/PVA), poly(N-vinylpyrrolidone) (PVP), poly(methyl methacrylate-co-hydroxyethyl methacrylate) (P(MMA-co-HEMA)), poly(polyethyleneglycol-co-peptide) (P(PEG-co-peptide)), alginate-g-(polyethylene oxide-polypropylene oxide-polyethylene oxide) (alginate-g-(PEOPPO-PEO)), poly(polylactic acid-co-glycolic acid)-co-serine) (P(PLGA-co-serine)), collagenacrylate, alginate-acrylate, poly(hydroxypropyl methacrylamide-g-peptide) (P(HPMA-g-peptide)), poly(hydroxyethyl methacrylate/matrigel) (P(HEMA/Matrigel)), hyaluronic acid-g-N-isopropylacrylamide (HA-g-NIPAAm), polyethylene oxide (PEO), a polyethylene oxide-polypropylene oxide copolymer (PEO-PPO, Pluronic series), a polyethylene oxide-polylactic acid copolymer (PEO-PLA), a polyethylene oxide-polylactic glycolic acid copolymer (PEO-PLGA), a polyethylene oxide-polycaprolactone copolymer (PEO-PCL), polyoxyethylene alkyl ethers (Brij Series), polyoxyethylene castor oil derivatives (Cremophores), polyoxyethylene sorbitan fatty acid esters (Tween Series), and polyoxyethylene stearates.

The keratin may stimulate hair regeneration.

The pharmaceutical composition may increase an expression level of at least one selected from the group consisting of beta-catenin, Sox-9, Sox-2, alkaline phosphatase, CD133, FGF7, FGF10, BMP6, P-cadherin, E-cadherin, MSX2, FOXN1 and CD10.

The pharmaceutical composition may be administered to the dermal layer or the subcutaneous tissue.

The pharmaceutical composition may further include a penetration enhancer.

The penetration enhancer may be selected at least one from the group consisting of sulphoxide, azone, pyrrolidone, fatty acids, lower alcohols having 1 to 4 carbon atoms, higher fatty alcohols having 6 or more carbon atoms, glycols, urea, terpene, terpenoid, and phospholipid.

The hydrolyzed keratin may be prepared by a preparation method of hydrolyzed keratin, including S1) reacting keratin with hydrolase; and S2) removing the hydrolase.

The hydrolase may be proteinase-K.

The hydrolase may be immobilized on beads.

The preparation method of hydrolyzed keratin may further include S3) removing the activity of the hydrolase after step S2).

Advantageous Effects

The injectable pharmaceutical composition containing keratin of the present invention stimulates hair growth and formation of hair follicles.

Furthermore, when the injectable pharmaceutical composition containing keratin of the present invention is injected into the skin tissue, it is more effective to stimulate hair growth or prevent hair loss than when the pharmaceutical composition is applied to the skin.

Therefore, the pharmaceutical composition of the present invention can be used as a therapeutic agent for preventing hair loss or stimulating hair growth.

DESCRIPTION OF DRAWINGS

FIG. 8 is a photograph of confirming that keratin is attached to the cell surface by analyzing interaction with cells and then formation of cell aggregates is induced by keratin, when human dermal papilla cells are treated with keratin.

FIG. 9 is a diagram illustrating that expression of mRNA associated with cell proliferation is suppressed and expression of mRNA associated with cell migration, induction of cell aggregates, and synthesis of an extracellular matrix is increased, when human dermal papilla cells are treated with keratin.

FIG. 10 is a diagram illustrating that molecular expression of FGF7, FGF10 and BMP6, which are known as factors inducing hair growth, is increased when human dermal papilla cells are treated with keratin.

FIG. 14 is a graph illustrating that expression of a Sox-9 gene and a beta-catenin gene involved with stemness is increased when outer root sheath cells are treated with hydrolyzed keratin.

FIG. 15 is a graph of confirming that a beta-catenin molecule is expressed four times or more when outer root sheath cells are treated with hydrolyzed keratin.

MODE FOR INVENTION

Figure 1:
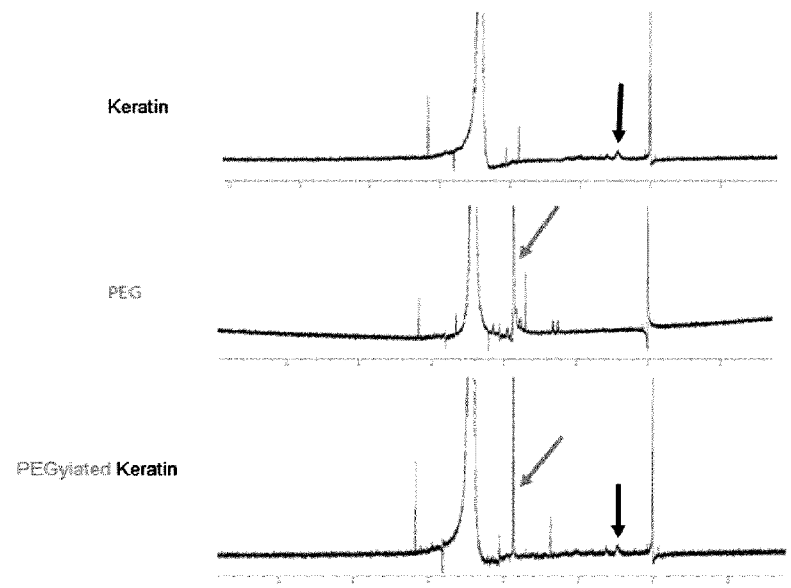
FIG. 1 illustrates data obtained by NMR analysis of PEGylated keratin.

The present invention provides an injectable pharmaceutical composition containing keratin for preventing hair loss or stimulating hair growth.

The keratin may be a true keratin constituting hair, fleece, feather, horn, nail, horseshoe, or the like, and may be keratin existing in the skin, nervous tissue or the like.

In addition, the keratin includes amino acids such as glutamic acid, arginine, and cystine, and particularly may contain a high content of cystine.

The keratin may be any commercially available keratin, processed to be soluble in water or a water-soluble solvent, preferably, human hair-derived keratin, and the molecular weight thereof may be 40,000 to 70,000 Daltons.

The keratin may be hydrolyzed keratin or keratin linked to a water-soluble polymer.

The hydrolyzed keratin is a protein that exhibits water solubility by decomposing insoluble natural keratin while retaining the properties of keratin, and may be used in combination with keratin-derived peptides. The hydrolyzed keratin may be prepared by hydrolyzing keratin with acid, alkali, oxygen, or hydrolase, but is not limited thereto, and may be obtained by a general method of preparing a hydrolyzed keratin having a molecular weight of 500 to 10,000 Daltons from natural keratin.

The hydrolyzed keratin may be prepared by a preparation method of hydrolyzed keratin, including S1) reacting keratin with a hydrolase; and S2) removing the hydrolase.

The step S1) is a step of preparing keratin hydrolyzed from keratin using the hydrolase.

Here, the hydrolase is classified into 9 groups according to their action targets, as groups classified into enzymes that catalyze hydrolysis reactions when enzymes are classified systematically.

The hydrolase is an enzyme which may hydrolyze natural keratin because the keratin is a protein, and preferably an enzyme that acts on peptide bonds. Specifically, the enzyme that acts on the peptide bonds may be any one selected from proteases including Leucyl aminopeptidase, carboxypeptidase, pepsin, trypsin, and chymotrypsin. More preferably, the enzyme is a proteinase-K, but is not limited thereto.

In the method for preparing the hydrolyzed keratin, if the step S1) is absent or is not properly performed, the yield of the hydrolyzed keratin exhibiting an effect of preventing hair loss or stimulating hair growth may be insufficient.

Next, the step S2) is a step of obtaining only the hydrolyzed keratin from a mixture of the hydrolase and the hydrolyzed keratin. The hydrolase may be immobilized on beads. The hydrolase may be separated from the hydrolyzed keratin according to the physical/chemical properties of the bead using a difference in magnetism of the bead, a difference in weight, a difference in adsorption, or the like.

The beads may be selected at least one from the group consisting of poly-L-lactic acid (PLLA), a poly-lactic acid-glycolic acid copolymer (PLGA), polyglycolic acid (PGA), polyurethane (PU), polymethylmethacrylate (PMMA), polyethylene (PE), and ferromagnetite, but the present invention is not limited thereto. Specifically, the beads may be agarose beads.

In the method for preparing the hydrolyzed keratin, if the step S2) is absent or is not properly performed, the purity of the hydrolyzed keratin exhibiting an effect of preventing hair loss or stimulating hair growth may be lowered.

In addition, the method for preparing the hydrolyzed keratin may further include S3) removing the activity of the hydrolase, after the step S2).

The step S3) is for stopping the hydrolysis reaction of the keratin by removing the activity of the hydrolase, and may be left at a high temperature for several hours so that the hydrolase does not react with the keratin.

In the method for preparing the hydrolyzed keratin, if the step S3) is included, the purity of the hydrolyzed keratin may be increased and the hydrolyzed keratin having a uniform molecular weight may be obtained.

For example, the hydrolyzed keratin may be obtained by mixing human hair with a mixture of chloroform and methanol in a ratio of 2:1 to remove lipid, stirring the mixture in a 2% peracetic acid solution for 12 hours, and then adding 5% 2-mercaptoethanol, 5 M urea, 2.6 M thiourea, and 25 mM Tris-HCl (pH 8.5), and reacting at 50 to 72 hours, but the present invention is not limited thereto.

In the present invention, the water-soluble polymer may be selected at least one from the group consisting of hyaluronic acid, polyethylene glycol (PEG), alginic acid, pectin, carrageenan, chondroitin sulfate, dextran sulfate, chitosan, polylysine, collagen, gelatin, carboxymethyl chitin, fibrin, dextran, agarose, pullulan, polyacrylamide (PAAm), poly(N-isopropylacrylamide) (P(NIPAAm-co-AAc)), poly(N-isopropylacrylamide-co-ethylmethacrylate) (P(NIPAAm-co-EMA)), polyvinyl acetate/polyvinyl alcohol (PVAc/PVA), poly(N-vinylpyrrolidone) (PVP), poly(methyl methacrylate-co-hydroxyethyl methacrylate) (P(MMA-co-HEMA)), poly(polyethyleneglycol-co-peptide (P(PEG-co-peptide)), alginate-g-(polyethylene oxide-polypropylene oxide-polyethylene oxide) (alginate-g-(PEOPPO-PEO)), poly(polylactic acid-co-glycolic acid)-co-serine) (P(PLGA-co-serine)), collagenacrylate, alginate-acrylate, poly(hydroxypropyl methacrylamide-g-peptide) (P(HPMA-g-peptide)), poly(hydroxyethyl methacrylate/matrigel) (P(HEMA/Matrigel)), hyaluronic acid-g-N-isopropylacrylamide (HA-g-NIPAAm), polyethylene oxide (PEO), a polyethylene oxide-polypropylene oxide copolymer (PEO-PPO, Pluronic series), a polyethylene oxide-polylactic acid copolymer (PEO-PLA), a polyethylene oxide-polylactic glycolic acid copolymer (PEO-PLGA), a polyethylene oxide-polycaprolactone copolymer (PEO-PCL), polyoxyethylene alkyl ethers (Brij Series), polyoxyethylene castor oil derivatives (Cremophores), polyoxyethylene sorbitan fatty acid esters (Tween Series), and polyoxyethylene stearates. Preferably, the water-soluble polymer may be polyethylene glycol or hyaluronic acid, but the present invention is not limited thereto.

In the present invention, the polyethylene glycol may be, for example, O-methyl-O'-succinylpolyethylene glycol, dibasic acid polyethylene glycol, α,ω-bis(2-carboxyethyl-polyethylene glycol, O,O'-bis(2-bromoethyl) polyethylene glycol, O,O'-bis(2-chloroethyl) polyethylene glycol, polyethylene glycol dimethylate, methoxypolyethylene glycol acetic acid, O-[2-(3-succinylamino)ethyl]-O'-methyl-polyethylene glycol, O-(2-bromoethyl)-O'-methylpolyethylene glycol, O-(2-chloroethyl)-O'-methylpolyethylene glycol, polyethylene glycol monomethyl ether mesylate, aldehyde-functionalized polyethylene glycol, glycidyl ether functionalized polyethylene glycol, nitrophenyl carbonate functionalized polyethylene glycol, mesyl functionalized polyethylene glycol, or tosyl functionalized polyethylene glycol, and preferably O-methyl-O'-succinylpolyethylene glycol.

The molecular weight of the water-soluble polymer may be 1000 Da to 4000 kDa, preferably 2000 Da to 3000 kDa. As a preferable example, hyaluronic acid of 1000 kDa to 4000 kDa or polyethylene glycol of 1000 Da to 20000 Da may be used.

The keratin may stimulate hair regeneration.

Specifically, the keratin may induce the growth of human outer root sheath cells or dermal papilla cells and the aggregation of cells to stimulate hair regeneration.

The "stimulation of hair growth" mentioned in the present invention means stimulating "hair growth" and/or "hair regeneration", the "hair regeneration" means inducing growth of human outer root sheath cells or dermal papilla cells or cell aggregation to ultimately prevent hair from falling out easily, and means inducing the formation of hair follicles by stimulating formation of hair follicles at an anagen stage which is an initial stage of hair growth to regenerate the hair. Furthermore, the "stimulation of hair growth" includes increasing expression factors involved to migration of human outer root sheath cells and activity of clones or stemness.

In addition, the pharmaceutical composition according to the present invention may increase the expression levels of genes for inducing hair regeneration and hair growth contained in human outer root sheath cells or dermal papilla cells.

The gene may be selected at least one from the group consisting of beta-catenin, SRY box transcription factor 9 (Sox-9), SRY box transcription factor 2 (Sox-2), alkaline phosphatase, prominin-1 (CD133), fibroblast growth factor 7 (FGF7), fibroblast growth factor 10 (FGF10), bone morphogenetic protein 6 (BMP6), P-cadherin, E-cadherin, msh homeobox 2 (MSX2), forkhead box N1 (FOXN1) and neprilysin (CD10).

The beta-catenin means a signaling substance that receives a signal of a Wnt protein to migrate into the cell nucleus and regulates the expression of a target gene involved in cell proliferation and differentiation, a substance which is contained in stem cells to be grown to hair, and a substance related with cell migration and clonal activity.

The Sox-9 is a substance involved in stemness and means a gene expressed in the nucleus of outer root sheath (ORS) and sebaceous gland cells of hair.

The Sox-2 means a substance which is highly expressed in embryonic stem cells, plays an important role not only in maintaining the pluripotency of embryonic stem cells but also in making inducing pluripotent stem cells, and has an important function for maintaining stem cell characteristics.

The alkaline phosphatase as a kind of enzyme is a substance which exists in various part of body as several isoenzymes, a substance involved in angiogenesis in a hair matrix during hair growth and means a substance of which activity is increased when hair growth occurs.

The CD133 is known as a protein which exists in the extracellular membrane and is induced to be expressed when the cells grow, corresponds to a cluster of differentiation (CD)-based protein, and means a substance which may have immunological properties of hair follicle stem cells.

The FGF7 is a keratinocyte growth factor and means a substance that penetrates into the dermis below the epidermis to strongly stimulate the growth and proliferation of keratinocytes.

The FGF10 is a fibroblast growth factor and means a substance that penetrates into the dermis below the epidermis to strongly stimulate the growth and proliferation of fibroblasts.

The BMP6 is a protein that regulates biological activity in various kinds of cells including nerve cells and means a factor for inducing the formation of aggregates of human dermal papilla cells to induce hair growth.

The P-cadherin and E-cadherin as cadgerin-based proteins mean proteins which are used to attach cells, are linked to the actin cytoskeleton to have a function of help in assembling the proteins and acts as signaling molecules that change gene expression in cells, and mean factors involved in migration of human outer root sheath cells and differentiation into matrix cells.

The MSX2, FOXN1, and CD10 mean factors involved in the differentiation of human outer root sheath cells into matrix cells.

The pharmaceutical composition may increase beta-catenin or Sox-9 in human outer root sheath cells to induce migration of outer root sheath cells and activity of clones.

The pharmaceutical composition may stimulate the formation of cell aggregates of human dermal papilla cells and increase the formation of cell aggregates to induce hair growth and improve a hair regeneration effect.

The pharmaceutical composition may increase the expression of beta-catenin, Sox-2, alkaline phosphatase, CD133, FGF7, and FGF10 in human dermal papilla cells, thereby increasing the stemness of human dermal papilla cells.

In one specific embodiment of the present invention, the hair of the dorsal part of the elderly mouse with reduced physical functions was shaved and then a keratin solution was injected into the dorsal part to analyze the density of the growing hair and the formation of hair follicles. As a result, it was confirmed that the keratin stimulated the formation of hair follicles and hair regeneration. Thus, it has been seen that the keratin may be used in the injectable pharmaceutical composition for preventing hair loss or stimulating hair growth.

In the present invention, the term "injection" refers to the injection of a drug solution intradermally, subcutaneously, intramuscularly or intraarterially using a syringe. Specifically, since the pharmaceutical composition of the present invention has the effect of preventing hair loss or stimulating hair growth, the injection may be a subcutaneous injection, but is not limited thereto. The syringe can be used not only as a general syringe capable of administering a drug solution through a needle but also as a syringe used for subcutaneous administration of the pharmaceutical composition of the present invention.

In the present invention, the injectable pharmaceutical composition may be in the form of a liquid or dry powder. The dry powder for injection may be reconstituted with at least one selected from the group consisting of water for injection, a physiological saline solution, a glucose solution, and an amino acid solution to be administered to a subject.

The amount of an active ingredient contained in the composition of the present invention depends on a condition of a subject to be administered, a desired degree of treatment, and the like. Specifically, the keratin of the present invention may be contained in a concentration of 0.001 to 10 (w/v) %, specifically 0.01 (w/v) % to 5 (w/v) %, and more specifically 0.05 to 2 (w/v) % based on the injectable pharmaceutical composition.

When the concentration of the keratin is less than 0.001 (w/v) %, the effect of preventing hair loss or stimulating hair growth may be insufficient, and if the concentration of keratin is more than 10 (w/v) %, there is a problem that side effects in the body may be shown.

In the present invention, the composition may further include a penetration enhancer.

The pharmaceutical composition may be administered locally to a hair loss site or a site where hair growth is to be stimulated, preferably may be administered to the dermal layer or subcutaneous tissue. At this time, the dermal layer is the thickest layer below the epidermis, which means a layer where a vascular system, a nervous system, a lymphatic system, etc. are intricately intertwined, hair follicles are generated and grow, and hair follicles are contained.

The subcutaneous tissue is a portion between the muscle and the bone below the dermal layer, which has fat cells containing a large amount of fat to give the softness to the body softness, have the contour, and be used as energy. It also means that arteries and lymph are circulating.

The penetration enhancer may be at least one selected from the group consisting of sulphoxide, azone, pyrrolidone, fatty acids, lower alcohols having 1 to 4 carbon atoms, higher fatty alcohols having 6 or more carbon atoms, glycols, urea, terpene, terpenoid, and phospholipid. However, the penetration enhancer is not limited thereto and may include general stimulators that are used in the injectable pharmaceutical composition to stimulate transdermal penetration of an active ingredient.

The sulphoxide may be at least one selected from the group consisting of dimethyl sulfoxide (DMSO), dimethyl acetamide (DMAC), dimethyl formamide (DMF), and decylmethyl sulfoxide (DCMS), but is not limited thereto.

The pyrrolidone may be at least one selected from the group consisting of N-methyl-2-pyrrolidone (NMP) and 2-pyrrolidone (2P) but is not limited thereto.

The azone may be 1-dodecylazacycloheptan-2-one or laurocapram.

The penetration enhancer may be contained in a generally acceptable amount to the injectable composition depending on a kind to be used.

The pharmaceutical composition of the present invention may be used alone or in combination with hormonal therapy, chemotherapy, and methods using a biological response modifier for preventing hair loss or stimulating hair growth.

The present invention provides a method for preventing hair loss or stimulating hair growth including preparing an injectable pharmaceutical composition containing keratin; and administering the injectable pharmaceutical composition to a subject.

The "administration" means introducing a desired substance into the subject in an appropriate manner. In the present invention, the composition may be administered to the dermal layer or the subcutaneous tissue because of its characteristic of preventing hair loss or stimulating hair growth by injecting into the subject.

The pharmaceutical composition of the present invention varies depending on various factors including the activity of a specific compound used, age, weight, general health, gender, diet, time of administration, route of administration, rate of excretion, drug combination, and the severity of a specific disease to be prevented or treated. The dose of the pharmaceutical composition may vary depending on a condition of the patient, a body weight, the degree of disease, a type of drug, and route and period of administration, but may be suitably selected by those skilled in the art and may be administered in an amount of 0.0001 to 100 mg/kg or 0.001 to 100 mg/kg. The administration may be performed once a day or several times a day. The dose does not limit the scope of the present invention in any aspect. In addition, the dose and concentration may vary depending on the human hair growth area, and the concentration of the composition is preferably 0.1 to 100 mg/ml but is not limited thereto.

The "subject" means all animals such as mice, rats, and livestock, including humans that have or may develop hair loss symptoms. Specifically, the subject may be mammals including humans.

Hereinafter, preferred Preparation Examples or Experimental Examples are presented in order to assist understanding of the present invention. However, the following Preparation Examples or Experimental Examples are just provided to more easily understand the present invention and contents of the present invention are not limited by the embodiment.

Preparation Example 1: Obtainment of Keratin

Human hair was cleanly washed with a weak detergent and rinsed several times with distilled water. For lipid removal, the hair was placed in a beaker and added with a mixture of chloroform and methanol at a ratio of 2:1 until the hair sank. After 24 hours, the solution used for lipid removal was washed several times with distilled water until the solution was not left in the hair, and then the hair was air-dried. 20 g of the hair which had been air-dried was added in 800 mL of 2% acetic acid (Sigma aldrich), and the mixture was stirred at 37° C. for 12 hours at 300 rpm. After 12 hours, the hair was sieved and washed with distilled water to remove remaining oxides. The hair was added in a 400 mL Shindai solution (5% 2-mercaptoethanol, 5 M of urea, 2.6 M of thiourea (Sigma aldrich) and 25 mM Tris-HCl (pH 8.5)) and reacted for 72 hours under conditions of 50° C. and 400 rpm. Thereafter, the hair solution was added in a 50 mL tube and centrifuged at 3500 rpm for 20 minutes. The supernatant was collected and dialyzed using a 12-14 kDa cut-off Spectra/Por® 4 dialysis membrane (Spectrum). The dialyzed keratin liquid sample was lyophilized to prepare a keratin powder.

Preparation Example 2: Preparation of Hydrolyzed Keratin

First, $dH_2O$ was added to a brown vial (10 ml, 22*48) made of polyethylene terephthalate having a screw cap and 20 mg of Tritirachium album-derived proteinase K (immobilized to Eupergit®, Sigma-Aldrich) was added and dissolved at a concentration of 2 mg/ml. The proteinase-K was fully dissolved and then 400 mg of the keratin powder prepared according to Preparation Example 1 was weighed using an electronic balance for measurement of fine part unit count (0.001 g to 620 g, AJ-620E) and added into the vial. The vial was placed in a digital drying oven and then stirred at 37° C. at rate of 300 rpm for 1 hour using an egg-white, 5×2 mm magnetic stir bar (B00C3ME4ZA, 1572500 IKA-FLON 40, IKA) and a mobile MS-H-S10 10-Channel magnetic stirrer. The fully hydrolyzed keratin solution was placed in a centrifuge and operated at 250 g for 10 min to precipitate Proteinase-K immobilized Eupergit C and then the precipitate was removed. Only the supernatant was obtained and was added to an Eppendorf® PCR tube by 10 μl. The tube was boiled for 1 hour at 99° C. in CFX96 Touch™ Real-Time PCR detection system equipment to remove the activity of the proteinase-K. The hydrolyzed keratin liquid sample was lyophilized to prepare a hydrolyzed keratin powder.

Preparation Example 3: Preparation of PEGylated Keratin

Preparation Example 3-1: Synthesis of PEGylated Keratin

First, 0.5 g of the keratin powder obtained in Preparation Example 1 was weighed using an electronic balance (0.001 g to 620 g, AJ-620E) for measurement of fine part unit count and placed in a 500 mL Pyrex beaker (ISOLAB, YLS, Germany). 100 mL of tertiary water was added to a beaker and stirred at a rate of 300 rpm for 24 hours using a 40×8 mm magnetic stir bar (BOOC3ME4ZA, 1572500 IKAFLON 40, IKA) and an MS-H-S10 10-Channel magnetic stirrer.

300 mg of O-methyl-O'-succinyl polyethylene glycol 5000 (mPEG, 17929-5G-F, Lot #R063737/2V Sigma aldrich) modified with methoxypolyethylene glycol was dissolved in 20 mL of tertiary water for 1 hour. 16 mg of 4-(4,6-dimethoxy-1,3,5-triazin-2-yl)-4-methoxy morpholinium chloride (DMTMM) n-hydrate (327-53752, wako chemical) was added to an mPEG solution and then stirred for 1 hour. The keratin solution and a binding solution of mPEG and DMTMM were placed in a 500 mL beaker and stirred at a rate of 500 rpm at room temperature for 3 days using a 40×8 mm magnetic stir bar (1572500 IKAFLON 40, IKA) and an MS-H-S10 10-Channel magnetic stirrer.

Preparation Example 3-2: Purification of PEGylated Keratin

After the reaction of Preparation Example 3-1 was completed, the PEGylated keratin solution was added to a Spectra/Por permeable membrane tube (diameter of 16 mm, 25 mm of flat width, MW10000, Spectrum) by 100 mL per tube and packed using a Spectra/Por RC dialysis tubing closure (maximum width of 55 mm, Orange, Spectrum). A 5 L plastic beaker (197 mm in diameter, 265 mm in height) was filled with 4 L of tertiary water, added with the tube containing the PEGylated keratin solution, added with a magnetic bar, and stirred to perform dialysis. At this time, new tertiary water was changed every 12 hours and the dialysis was performed while the tertiary water was changing a total of 6 times at room temperature for 3 days. The final PEGylated keratin solution was placed in a 50 mL centrifuge tube (17×120 mm, BD Falcon) to be divided by 40 mL, and then completely frozen at −70° C. for 24 hours in a cryogenic refrigerator (Nihon freezer, Upright type, Single cooling type, 5421). The lid of the centrifuge tube was opened and the PEGylated keratin solution was placed in a freeze dryer (ALPHA 2-4 LSC PLUS, Laboratory freeze dryers, Christ) and dried for 3 days in a vacuum state at −85° C. to be completely powdered. Next, the PEGylated keratin was analyzed by NMR. As a result, as illustrated in FIG. 1, it was confirmed that the NMR spectra of the PEGylated keratin had signature peaks for keratin and PEG.

Preparation Example 3-3: Preparation of PEGylated Keratin Solution Containing Hydrogen Peroxide 20 mg of the PEGylated keratin obtained in Preparation Example 3-2 was measured using an electronic balance ((0.001 g to 620 g) AJ-620E) for measurement of fine part unit count. 102 μl of $H_2O_2$ (hydrogen peroxide 30%, molecular weight 34.01, JUNSEI CHEMICAL, 7722-84-1) was added to 898 μl of tertiary distilled water to make 1 mL of 1 M concentration, and then serial dilution was performed with distilled water 100 times and 20 times to prepare a final 500 uM of $H_2O_2$ solution. The prepared 500 uM of $H_2O_2$ solution was added with 20 mg of the PEGylated keratin and vortexed for 5 minutes to prepare a PEGylated keratin solution containing 500 uM $H_2O_2$. A glass bottle containing the prepared solution was sealed with a nylon vacuum packing machine 150×200 mm (NY/PELLDPE) (80 um) using a pneumatic vacuum packing machine and then stored.

Experimental Example 1: Hair Growth Effect in Animal Experiment

Experimental Example 1-1: Preparation of Animal Model

Twenty-four C57BL/6J aged mice (Charles River Corp. Inc., Barcelona, Spain) weighing 20 to 25 g, aged 12 weeks, were used as an animal model to verify a hair growth effect of keratin. After the mice were anesthetized with isoflurane, the dorsal parts of the mice were shaved with a clipper, and the hair and root were shaved while leaving a telogen stage hair root. The skin was disinfected with a povidone-iodine solution and then wiped with 60% alcohol.

Experimental Example 1-2: Hair Growth Effect of Keratin

Figure 2:
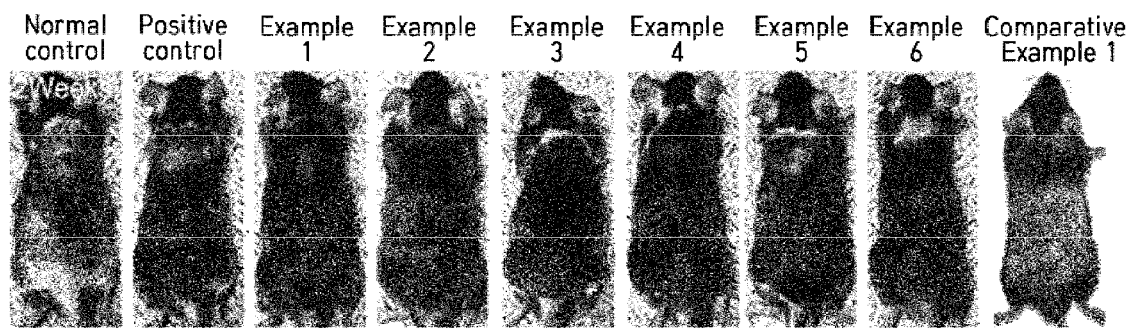
FIG. 2 is a diagram illustrating a hair growth effect, 2 weeks after injecting Examples 1 to 6 into hair-removed mice.

The dorsal parts of the mice prepared according to Experimental Example 1-1 were administered and prepared as illustrated in Table 1 below. A normal control group was a mouse that had not been subjected to any treatment after hair cutting. All mice were bred for 2 weeks, and at 2 weeks, hair cut areas were observed with a stereomicroscope (SZX16, Olympus). The results were illustrated in FIG. 2.

TABLE 1

| Classification | Ingredient | Administration method |
| --- | --- | --- |
| Normal control group | — | — |
| Positive control group | 3% minoxidil | Apply on the skin daily for 2 weeks (application amount 100 μl/cm²) |
| Example 1 | 0.5 w/v % of keratin-containing solution obtained from Preparation Example 1 | Subcutaneous single injection (300 μl) |
| Example 2 | 1 w/v % of keratin-containing solution obtained from Preparation Example 1 | Subcutaneous single injection (300 μl) |
| Example 3 | 0.5 w/v % of hydrolyzed keratin-containing solution obtained from Preparation Example 2 | Subcutaneous single injection (300 μl) |
| Example 4 | 1 w/v % of hydrolyzed keratin-containing solution obtained from Preparation Example 2 | Subcutaneous single injection (300 μl) |
| Example 5 | 0.5 w/v % of PEGylated keratin-containing solution obtained from Preparation Example 3-2 | Subcutaneous single injection (300 μl) |
| Example 6 | 0.5 w/v % of PEGylated keratin-containing solution obtained from Preparation Example 3-2 | Subcutaneous single injection (300 μl) |
| Comparative Example 1 | 1 w/v % of keratin-containing solution obtained from Preparation Example 1 | Apply on the skin (application amount 100 μl/cm²) |

As a result, it was shown that in Examples 1 to 6, a hair growth effect was remarkably superior to that in the normal control group, and in Examples 1 to 6, hair was uniformly grown and in Examples 1, 2 and 4, the hair was very densely grown. Accordingly, it was confirmed that when the keratin was subcutaneously injected, the hair growth effect was better than that when the keratin was applied on the skin, it was confirmed that the injectable pharmaceutical composition containing keratin according to the present invention had effects of preventing hair loss and stimulating hair growth, and it was confirmed that the effects of preventing hair loss and stimulating hair growth were fast.

In addition, the injectable pharmaceutical composition containing the keratin of the present invention had a remarkably high effect of preventing hair loss and stimulating hair growth than when a formulation was applied to the skin as a conventional external preparation for skin, and the subcutaneous injection using the formulation as an injectable product had a higher bioavailability.

On the other hand, when the formulation was converted into an injection other than the external preparation for skin, side effects such as toxicity were also increased due to an increase in bioavailability when used as an injection as compared with when used as an external preparation for skin, and thus it is also important to solve the side effects. Therefore, it was confirmed through FIG. 2 that the injectable pharmaceutical composition containing the keratin of the present invention had no toxicity at the time of subcutaneous injection of the injectable pharmaceutical composition containing keratin, and after subcutaneous injection of the pharmaceutical composition, there were no side effects that occurred by reacting with blood or moisture in the body.

Figure 4:
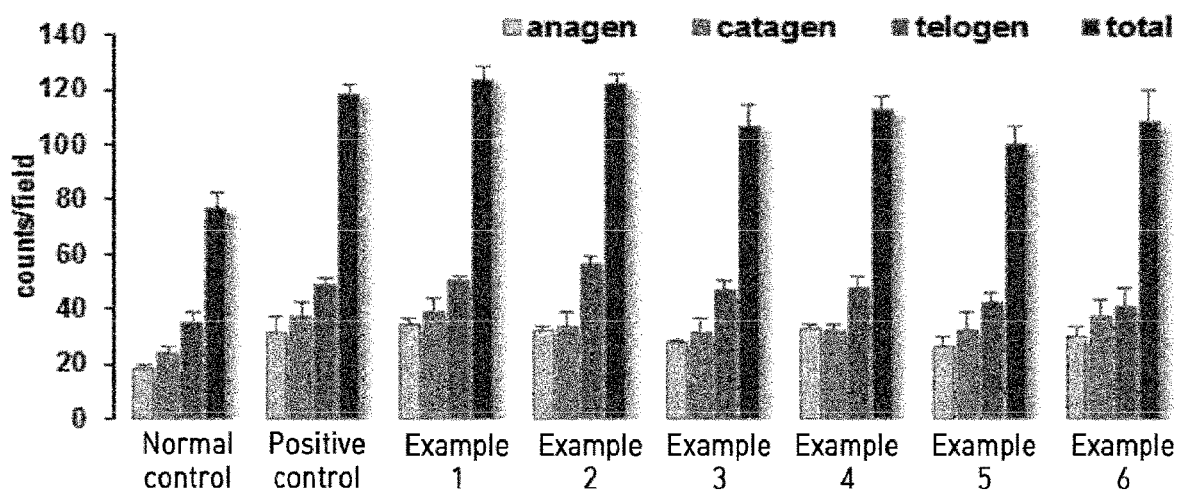
FIG. 4 is a graph illustrating the number of hair follicles formed in each stage of hair growth, 2 weeks after injecting Examples 1 to 6 into hair-removed mice.
Figure 5:
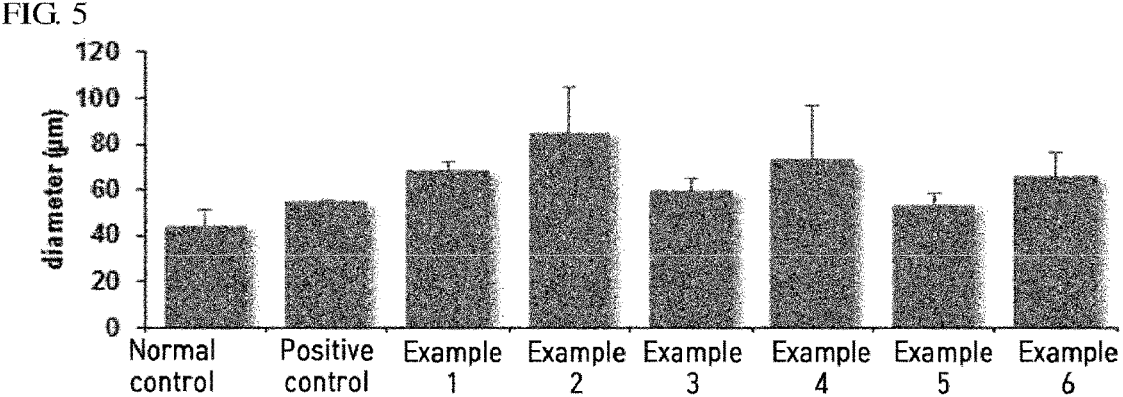
FIG. 5 is a graph illustrating sizes of hair follicles formed, 2 weeks after injecting Examples 1 to 6 into hair-removed mice.

Experimental Example 1-3: Histological Analysis of Hair Growth Effect of Keratin After completion of Experimental Example 1-2, tissue specimens were obtained by sacrificing the mice to which the solutions of Examples 1 to 6 were administered, a normal control and a positive control, respectively. The tissue specimens were stained with hematoxylin and eosin (H&E), observed, and analyzed and the results are illustrated in FIGS. 3 to 5.

Figure 3:
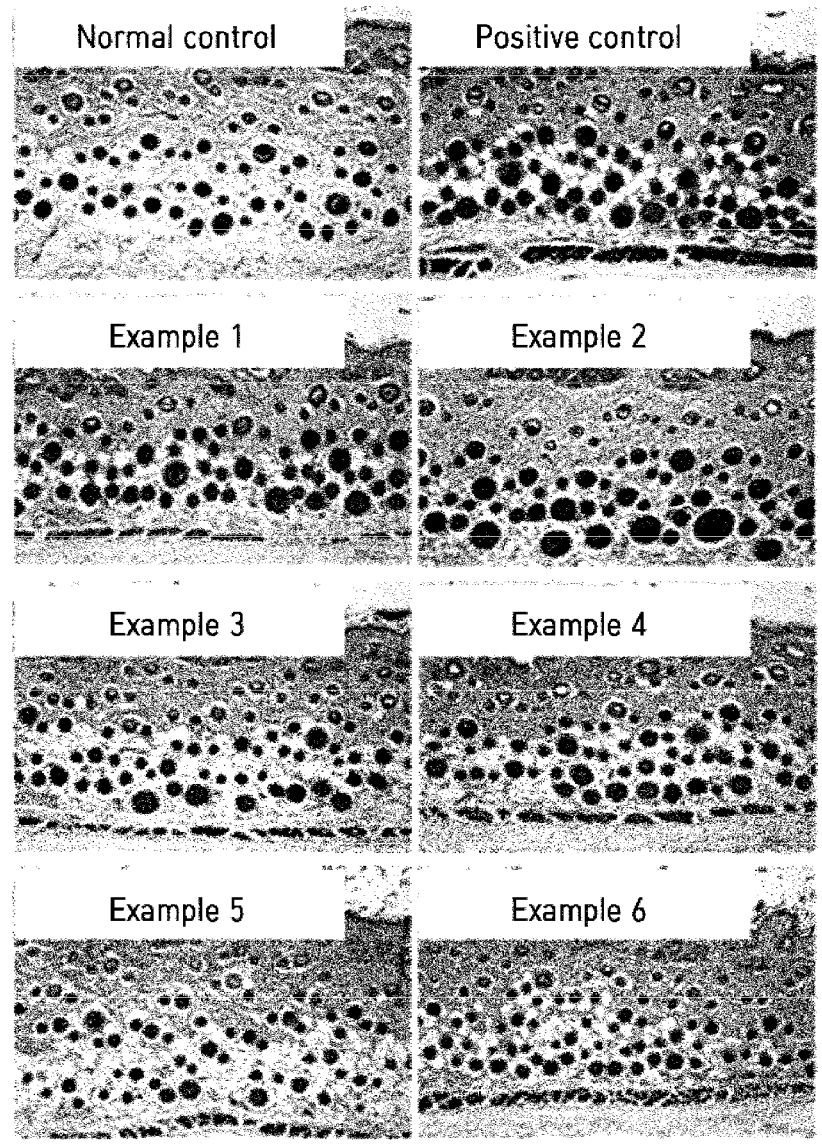
FIG. 3 is a photograph illustrating the degree of hair follicle formation by injecting Examples 1 to 6 into hair-removed mice and then staining the injected mice with hematoxylin-eosin after 2 weeks.

As a result, it was confirmed that formation of hair follicles occurred in mice administered with the keratin solutions of Examples 1 to 6 at a much higher frequency than the normal control (FIG. 3). In particular, it was confirmed that in the mice administered with the keratin and hydrolyzed keratin solutions of Examples 1 to 4, the hair follicle size was increased as compared with the mice to which the PEGylated keratin solutions of Examples 5 to 6 was administered. Specifically, as illustrated in FIG. 4, as a result of the analysis of each stage of hair growth, it was confirmed that the formation of hair follicles was stimulated in an anagen stage, which is an early stage of hair growth, and as a result, formation of new hair follicles was induced (FIG. 4). In addition, as the concentration of the keratin solution administered to the mice increased, the diameter of hair follicles tended to increase (FIG. 5).

Experimental Example 2: Identification of Hydrolyzed Keratin

Figure 6:
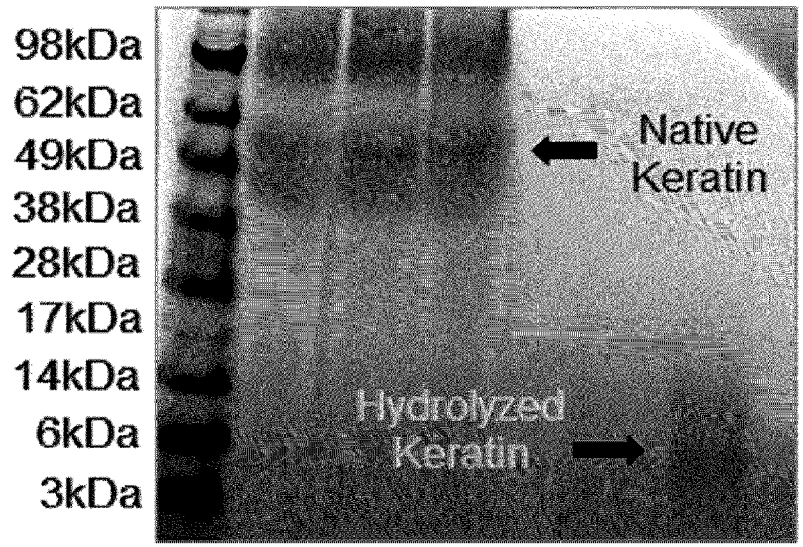
FIG. 6 is a photograph of a result of SDS-PAGE analysis for confirming that hydrolyzed keratin having a different molecular weight from natural keratin may be prepared.

Whether the hydrolyzed keratin was prepared according to Preparation Example 2 was identified by SDS-PAGE and illustrated in FIG. 6.

Specifically, a SeeBlue® plus 2 Pre-Stained Standard (novex) size marker was taken out at room temperature and the solution was vortexed to be completely mixed. A total of 40 μl of a sample obtained by mixing 10 μl of Bolt™ LDS Sample Buffer (4×), 4 μl of Bolt™ LDS Reducing Agent (10×), and 26 μl of 4% hydrolyzed keratin was vortexed. A hydrolyzed keratin sample was prepared by setting the temperature of a heating block (HYSC_Introduction_Heating Block_2014) at 100° C. and heating for 10 minutes. After a comb portion of a Bolt Bis-Tris 4-12% gradient mini gel (Invitrogen) was removed, wells were washed with a 1×MES running buffer and a cover tape at the end of a cassette was removed. Before loading the sample, a chamber of the cassette was filled with the 1×MES running buffer and locked with a cassette clamp to prevent the buffer from being removed. The wells to which the sample was to be loaded were filled with the 1×MES running buffer. 30 μl of a 4% hydrolyzed keratin sample and 10 μl of a SeeBlue® plus2 Pre-Stained Standard (novex) size marker were loaded, respectively. 0.012, 0.015, and 0.020 mg/600 μl PAA keratin samples were used as a control. The cassette was filled with the 1×MES running buffer by an outer scale, loaded with the size marker and the 4% hydrolyzed keratin sample, and then run at 165V for 40 minutes with a PowerPac™ Basic Power Supply (Bio-rad). After running, the cassette clamp was released and only the loaded gel was obtained and stained with Comassie brilliant blue G-250 (Sigma) for 24 hours. The size marker and the protein were identified after washing with a destain solution (10% (v/v) acetic acid, 40% (v/v) methanol) until the band was visible.

As a result, as illustrated in FIG. 6, it was confirmed that in the case of natural keratin extracted from the SDS-PAGE analysis result, a protein band was shown at a molecular weight level of about 50 k Daltons, but in the case of hydrolyzed keratin, a band was smearly shown at a molecular weight level of 3 to 6 k Daltons. As a result, it can be seen that the hydrolyzed keratin is constituted by various molecular weights of degraded peptides.

Experimental Example 3: Induction of Cell Aggregates and Expression Induction of Hair Growth-Related Factors of Keratin for Human Dermal Papilla Cells In Vitro In order to confirm a hair regeneration effect of keratin, expression of factors related to hair growth and induction of aggregation and hair growth was confirmed.

It was confirmed whether a keratin solution prepared using human dermal papilla cells showed efficacy in cell proliferation.

Specifically, human dermal papilla cells were inoculated on a 24-well plate by $2 \times 10^4$ cells, and after 24 hours, the medium was replaced with a DMEM normal medium at a high concentration or a DMEM normal medium containing 1% (w/v) of keratin at a high concentration. After 1, 3, and 5 days of culture, cell proliferation assay was performed. After the wells were washed with DPBS, a Cell Counting Kit-8 solution (Dojindo laboratory) 10-fold diluted with the high-concentration DMEM normal medium was added to each well, light was blocked with aluminum foil, and then the cells were incubated for 1 hour 30 minutes at 37° C. After incubation, 100 μl of each well was transferred to a 96-well plate and absorbance was measured at 450 nm wavelength (O.D 450 nm) using a 96-well format plate reader (ELX 800 universal microplate reader, BioTek, Inc.). The results were illustrated in FIG. 7.

Figure 7:
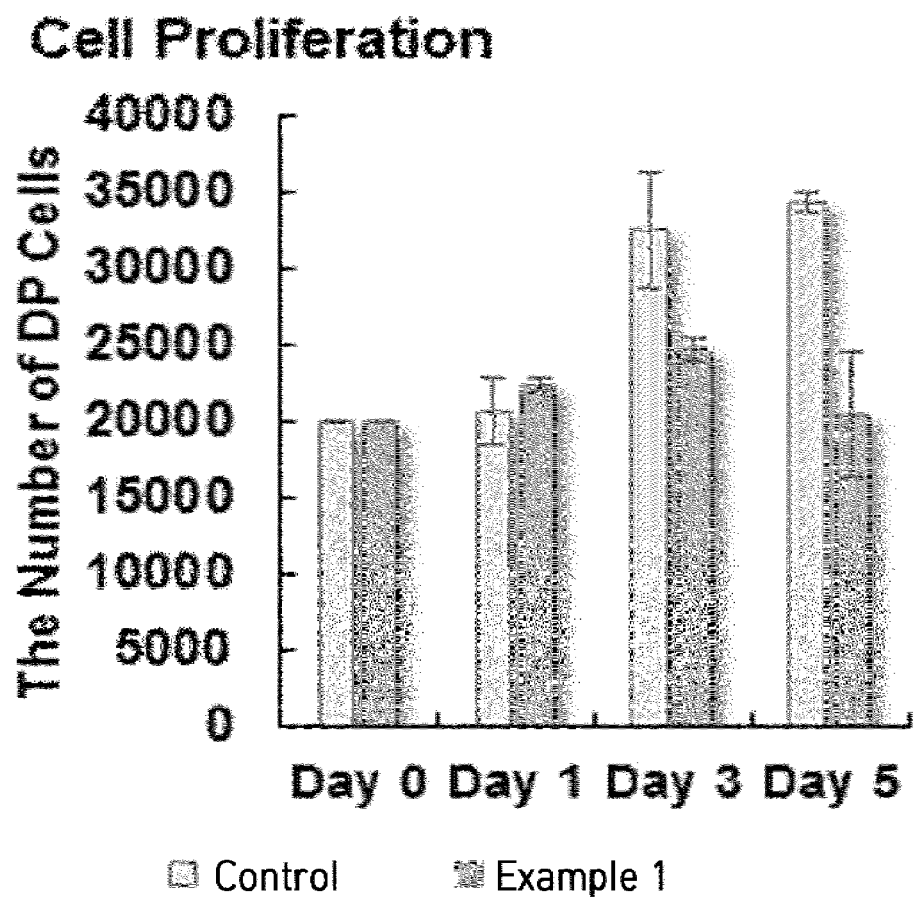
FIG. 7 is a diagram of confirming that cell proliferation is inhibited when human dermal papilla cells are treated with keratin.

As a result, it was found that the proliferation of human dermal papilla cells was inhibited during treatment of keratin (FIG. 7). In addition, after treatment of keratin complexed with a fluorescent substance, as a result of analyzing interaction with cells, it was confirmed that keratin was adhered to the cell surface, and formation of cell aggregates according to cell migration was induced by keratin over time (FIG. 8).

To further confirm these results by mRNA expression analysis, first, human dermal papilla cells were inoculated in a 6-well plate by $2 \times 10^5$ cells and after 24 hours, the medium was replaced with a DMEM normal medium at a high concentration or a DMEM normal medium containing 1% (w/v) of keratin at a high concentration. After keratin treatment for 24 hours, for RNA sequencing analysis, the culture medium of the cells cultured on the 6-well plate was removed and washed with DPBS. A hybrid-R kit (Gene All) was used for extracting RNA, and extracted RNA was quantified using a nano drop (MICROP UV-Vis Spectrophotometer M600). RNA sequencing analysis was performed by requesting 1 μg of RNA to Macrogen.

As a result, it was confirmed that expression of mRNA related to synthesis of an extracellular matrix and cell interactions involved in cell migration and induction of cell aggregates in keratin-treated human dermal papilla cells was greatly increased, and mRNA expression associated with cell proliferation was inhibited (FIG. 9).

Further, the human dermal papilla cells were inoculated on a 6-well plate by $2 \times 10^5$ cells, and after 24 hours, the medium was replaced with a DMEM normal medium at a high concentration or a DMEM normal medium containing 1% (w/v) of keratin at a high concentration. After 3 and 5 days of culture, the expression level of the factors for inducing hair growth was measured by immunochemical staining.

After the human dermal papilla cells were cultured as described above, the medium was removed and the cells were washed with DPBS. The cells were immobilized by treating 4% paraformaldehyde for 10 minutes and then washed again with DPBS. After immobilization, 0.1% triton X-100 was treated for 30 minutes to be permeabilized and 10% (w/v) normal goat serum (NGS) was treated for 1 hour. Thereafter, a rabbit anti-human beta-catenin antibody diluted at 1:200, a mouse anti-human FGF7 antibody, rabbit anti-human FGF7 antibody, a rabbit anti-human FGF10 antibody, and a rabbit anti-human BMP6 antibody were treated and reacted at 4° C. for 24 hours. After 24 hours of reaction, the cells were washed three times with DPBS, and a secondary Alexa Fluor 546 conjugated antibody and a secondary Alexa Fluor 488-conjugated antibody were treated at room temperature for 1 hour. Thereafter, the cells were washed three times with DPBS and treated with 4',6-diamidino-2-phenylindole (DAPI). The stained cells were then observed with a fluorescence microscope (Olympus I×71). As a result, formation of cell aggregates was induced in keratin-treated human dermal papilla cells, and the molecular expression of FGF7, FGF10 and BMP6, which were known as factors inducing hair growth, was greatly increased (FIG. 10).

Experimental Example 4: Expression induction of hair growth-related factors of keratin for human outer root sheath (ORS) in vitro In order to confirm a hair regeneration effect of keratin, expression of factors related to hair growth and induction of hair growth was confirmed.

It was confirmed whether a keratin solution prepared using human outer root sheath cells showed the expression of factors associated with hair growth and hair growth induction.

Specifically, the human outer root sheath cells were inoculated on a 6-well plate by 5×10$^4$ cells, and after 24 hours, the medium was replaced with an ORS medium or a 1% (w/v) keratin-containing ORS medium. After 3 days of incubation, the expression levels of beta-catenin, CD34, P-cadherin, and E-cadherin and the expression levels for transcription factors were measured by immunochemical staining and RT-PCR analysis.

After the human outer root sheath (ORS) cells were cultured as described above, the medium was removed and the cells were washed with DPBS. The cells were immobilized by treating 4% paraformaldehyde for 10 minutes and then washed again with DPBS. After immobilization, 0.1% triton X-100 was treated for 30 minutes to be permeabilized and 10% (w/v) normal goat serum (NGS) was treated for 1 hour. Thereafter, a rabbit anti-human beta-catenin antibody diluted at 1:200, a rabbit anti-human CD34 antibody, a rabbit anti-human P-cadherin antibody, a rabbit anti-human E-cadherin antibody, and a mouse anti-human integrin beta1 antibody were treated and reacted at 4° C. for 24 hours. After 24 hours of reaction, the cells were washed three times with DPBS, and a secondary Alexa Fluor 546 conjugated antibody, a secondary Alexa Fluor 488-conjugated antibody, and a PE-conjugated Palloidin antibody were treated at room temperature for 1 hour. Thereafter, the cells were washed three times with DPBS and treated with 4',6-diamidino-2-phenylindole (DAPI). The stained cells were then observed with a fluorescence microscope (Olympus I×71). For RT-PCR analysis, the culture medium of the cells cultured in the 6-well plate was removed and the cells were washed with DPBS. A hybrid-R kit (Gene All) was used for extracting RNA, and extracted RNA was quantified using a nano drop (MICROP UV-Vis Spectrophotometer M600). 1 μg of RNA was added to AccuPower Cycle Script RT Premix (Bioneer, Daejeon, Korea) and cDNA was prepared using a thermal cycler (T106, Bio-Rad). The sequences of primers used are illustrated in Table 2 below.

TABLE 2

| | Sense(5'-3') | Antisense(5'-3') |
|---|---|---|
| beta-catenin | TGCAGTTCGCCTTCACTATG (SEQ ID NO: 1) | CTGCACAAACAATGGAATGG (SEQ ID NO: 2) |
| KRT5 | ACCAGTACCCGCATCTGCA (SEQ ID NO: 3) | TGTTCCGTGGCCTCTTCG (SEQ ID NO: 4) |
| MSX2 | CCGCCAAGACATATGAGCCC (SEQ ID NO: 5) | ACCTGGGTCTCTGTGAGGTT (SEQ ID NO: 6) |
| ITGA6 | AGCTGTGCTTGCTCTACCTG (SEQ ID NO: 7) | CCGGGGTCTCCATATTTCCG (SEQ ID NO: 8) |
| FOXN1 | AGTGGTGCTGGGATGTTCTG (SEQ ID NO: 9) | ATAGTGTGAGGAGCCCAGGT (SEQ ID NO: 10) |
| CD10 | CTTTAGTGCCCAGCAGTCCA (SEQ ID NO: 11) | GAGTCCACCAGTCAACGAGG (SEQ ID NO: 12) |
| beta-actin | GTCAGGCAGCTCGTAGCTCT (SEQ ID NO: 13) | TCGTGCGTGACATTAAGGAG (SEQ ID NO: 14) |

To each reaction, 10 μl of SYBR Green PCR Mix, 0.5 pm of primers (sense and antisense) and 50 nm of a template were added. RT-PCR was performed using RG6000 5plex HRM (Corbett Research) instrument and 40 cycles were set at 95° C. for 15 seconds and annealing temperature of 57° C. for 45 seconds. A comparative quantification (Ct($2^{-\Delta\Delta Ct}$)) method was used to measure a threshold cycle (Ct) value.

Figure 11:
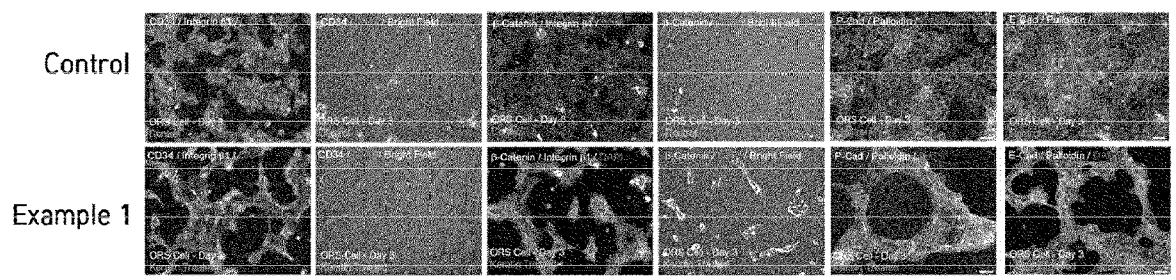
FIG. 11 is a graph of confirming that expression of beta-catenin and P-cadherin as factors related with cell migration and differentiation into matrix cells is increased and expression of CD34 as a molecule that reduces expression at differentiation is decreased, when human outer root sheath cells are treated with keratin.

As a result, in the case of the human outer root sheath (ORS) cells, in the treatment of keratin, it was confirmed that the expression of beta-catenin and P-cadherin, which were factors involved in migration of outer root sheath cells and differentiation into matrix cells in relation with hair regeneration, was increased, and the expression of CD34 known as a molecule of which expression was decreased in differentiation was reduced (FIG. 11).

Figure 12:
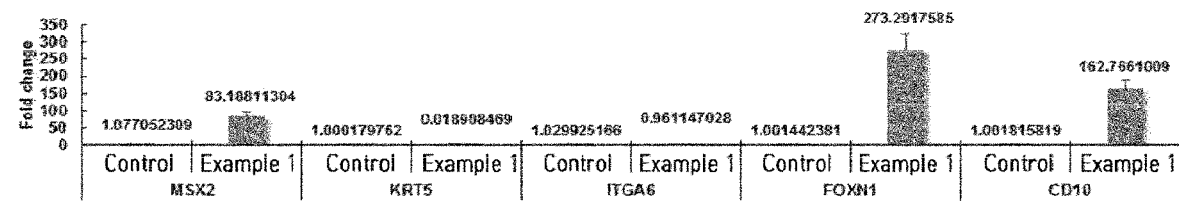
FIG. 12 is a graph of confirming that gene expression of MSX2, FOXN1, and CD10 as factors related with differentiation into matrix cells is increased and gene expression of KRT5 and ITGA6 as molecules with reduced expression at differentiation is decreased, when human outer root sheath cells are treated with keratin.

In addition, it was confirmed that the expression of MSX2, FOXN1 and CD10 genes associated with the differentiation of human outer root sheath (ORS) cells into matrix cells during keratin treatment was increased (FIG. 12), and the expression of KRT5 and ITGA6 genes known to be decreased in expression upon differentiation was decreased (FIG. 12).

Experimental Example 5: Expression Induction of Hair Growth-Related Factors of Hydrolyzed Keratin for Human Outer Root Sheath Cells In Vitro In order to confirm a hair regeneration effect of hydrolyzed keratin, the expression of factors related to hair growth and stemness was confirmed.

The human outer root sheath (ORS) cells were inoculated on a 6-well plate by 5×10$^4$ cells, and after 24 hours, the medium was replaced with an ORS medium or a 1% (w/v) hydrolyzed keratin-containing ORS medium. After 1, 3 and 5 days of culture, expression levels of beta-catenin, Sox-9, and CD44 were measured by immunochemical staining and RT-PCR analysis.

After the human outer root sheath (ORS) cells were cultured as described above, the medium was removed and the cells were washed with DPBS. The cells were immobilized by treating 4% paraformaldehyde for 10 minutes and then washed again with DPBS. After immobilization, 0.1% triton X-100 was treated for 30 minutes to be permeabilized and 10% (w/v) normal goat serum (NGS) was treated for 1 hour. Thereafter, a rabbit anti-human beta-catenin antibody diluted at 1:200, a rabbit anti-human Sox-9 antibody, and a rabbit anti-human CD44 antibody were treated and reacted at 4° C. for 24 hours. After 24 hours of reaction, the cells were washed three times with DPBS, and a secondary Alexa Fluor 546 conjugated antibody and a secondary Alexa Fluor 488-conjugated antibody were treated at room temperature for 1 hour. Thereafter, the cells were washed three times with DPBS and treated with 4',6-diamidino-2-phenylindole (DAPI). The stained cells were then observed with a fluorescence microscope (Olympus Ix71). For RT-PCR analysis, the culture medium of the cells cultured in the 6-well plate was removed and the cells were washed with DPBS. A hybrid-R kit (Gene All) was used for extracting RNA, and extracted RNA was quantified using a nano drop (MICROP UV-Vis Spectrophotometer M600). 1 µg of RNA was added to AccuPower Cycle Script RT Premix (Bioneer, Daejeon, Korea) and cDNA was prepared using a thermal cycler (T106, Bio-Rad). The sequences of primers used are illustrated in Table 3 below.

TABLE 3

|  | Sense(5'-3') | Antisense(5'-3') |
|---|---|---|
| beta-catenin | TGCAGTTCGCCTTCACTATG (SEQ ID NO: 1) | CTGCACAAACAATGGAATGG (SEQ ID NO: 2) |
| Sox-9 | ACCAGTACCCGCATCTGCA (SEQ ID NO: 15) | TGTTCCGTGGCCTCTTCG (SEQ ID NO: 16) |
| beta-actin | GTCAGGCAGCTCGTAGCTCT (SEQ ID NO: 13) | TCGTGCGTGACATTAAGGAG (SEQ ID NO: 14) |

To each reaction, 10 µl of SYBR Green PCR Mix, 0.5 µm of primers (sense and antisense) and 50 nm of a template were added.

RT-PCR was performed using RG6000 5plex HRM (Corbett Research) instrument and 40 cycles were set at 95° C. for 15 seconds and annealing temperature of 57° C. for 45 seconds. A comparative quantification (Ct($2^{-\Delta\Delta Ct}$)) method was used to measure a threshold cycle (Ct) value.

After the human outer root sheath (ORS) cells were cultured as described above, the medium was removed and the cells were washed with DPBS. 0.3 to 1 ml of a protein lysis buffer (Cell Lysis Buffer (10×): RiPA buffer (biorad-89901) and Phosphatase Inhibitor Cocktail (thermofisher (100×), 78440) was added and cells were collected with a scraper and transferred to an e-tube. A protein-containing supernatant was obtained by centrifuging the cells at 4° C. for 30 minutes using a centrifuge (Centrifuge 5427 R, effendorf 10,000×g). Protein quantification was performed using a Bio Rad Protein Assay reagent. 30 µg of a protein sample was added with a 6× sample dye (DTT, sigma 43815, bromophenol blue sigma, BR0222, Glycerl, bioshop, GLY001) and mixed to become 1×, and the sample was added to a heating block (HYSC_Introduction_Heating Block_2014) and heated at 95° C. for 10 minutes. PROTEAN® Tetra Handcast Systems (Bio-rad) were prepared by lightly spinning-down and vortexing (Stuart Scientific SA8 vortex mixer AC input 90/230 V, 50-60 Hz) the sample, and then leaving the sample in the ice. In order to prepare a gel, short glass and long glass were assembled in plates for hand casting, and a glass plate was washed with 70% ethanol (merk) and distilled water and then put in a frame, and a grease was applied to the bottom of the plate which hardened the gel to prevent the gel from leaking. A final 22 ml of separating gel (containing 6 ml of 30% acrylamide (30% Acrylamide/Bis Solution, 19:1 #1610154), 5 ml of dH$_2$O, 3.75 ml of 1.5 M Tris-HCl (Sigma, T1503), 150 µl of SDS (sigma, sodium dodecyl sulfite, L3771), 7.5 µl of TEMED (USB, 76230), and 75 µl of 10% ammonium persulfate (sigma, 215589)) was prepared and placed in a glass plate, and then added with 70% ethanol to be leveled. After about 30 minutes, the glass plate was tilted to remove ethanol, and then a final 10 ml of stacking gel (containing 1.3 ml of 30% acrylamide (30% Acrylamide/Bis Solution, 19:1 #1610154), 6.1 ml of dH$_2$O, 2.5 ml of 1.0 M Tris-HCl (Sigma, T1503), 100 µl of HCl (sigma, T1503), 10 µl of TEMED (USB, 76230), and 60 µl of 10% ammonium persulfate (sigma, 215589)) was prepared. The stacking gel was added, a 1.0 mm comb was inserted, and then the gel plate was set in an electrophoretic tank. A sample was loaded into each well and 5 µl of a size marker (ladder) (protein molecular weight marker 10 to 245 kDa ab116028-Abcam) was also added. A mini gel was reacted at 50V for 20 minutes and electrophoresed for 1 hour to 1.5 hours while increasing to 100V when passing through the stacking gel. After the electrophoresis was completed, the gel was separated from the gel plate and placed in a transfer buffer. Meanwhile, the transfer buffer was prepared using 14.4 g of Glycine (Sigma), 3 g of Trizma base (Sigma, T1503), 200 mL of methanol, and 800 mL of dH$_2$O. A PVDF transfer membrane (millipore cat No ISEQ 10100 10 cm×10 cm PVDF) was immersed in methanol for 5 minutes, in tertiary H$_2$O for 3 minutes and in a transfer buffer for 3 minutes and shaken, and then a cassette sandwich was made in the following order: (−) Black plate—Sponge—3M paper—Transparent plate transfer device (Bio-rad). The cassette was placed in a water bath and transferred at 200 V for 90 minutes on a stirrer. After the transfer was completed, the band was confirmed by dying the gel and the membrane. 2.5 g of ponceau S and 5 ml of acetic acid were added to dH$_2$O to prepare a reagent solution having a volume of 500 ml, and then the entire membrane was shaken in the reagent solution for about 5 minutes and then washed with H$_2$O 2 to 3 times, and as a result, the band was confirmed and the ladder size was displayed. A blocking solution was prepared with 10 g of skim milk (BD, 2322100) and 200 ml of TBS (Tris 12 g, NaCl 9 g in dH$_2$O), the membrane was placed in a plastic bowl, and then cells were incubated in 10 ml of the blocking solution for 1 hour. A B-catenin primary antibody (B-catenin antibody [E247] (ab32572)) and a B-Actin primary antibody (β-Actin Antibody (C4)) diluted at 1:1000 were added to 10 ml of the blocking solution and incubated in a Santa Cruz incubator at 4° C. for 24 hours. The cells were washed three times for 5 min each with TBST (Tris 12 g, NaCl 9 g in dH$_2$O, 1% tween 20) and a B-catenin secondary antibody (goat anti-rabbit IgG-HRP: sc-2004) and a B-Actin secondary antibody (mouse anti-rabbit IgG-HRP) diluted at 1:10000 were incubated in 10 ml of the blocking solution for 2 hours. The cells were washed three times for 5 min each with TBST (Tris 12 g, NaCl 9 g in dH$_2$O, 1% tween 20) and then ECL Substrate (Daemyung Science) was added and incubated for 5 minutes. In a dark room, a membrane was placed on a development cassette (Daemyung Science, High-Sensitivity Screen), an X-ray film (Daemyung Science 8×10 inch) was incubated for 5 minutes, and the film was taken out and developed on an automatic developing machine (SAEKI, P & C, ATL-1500).

Figure 13:
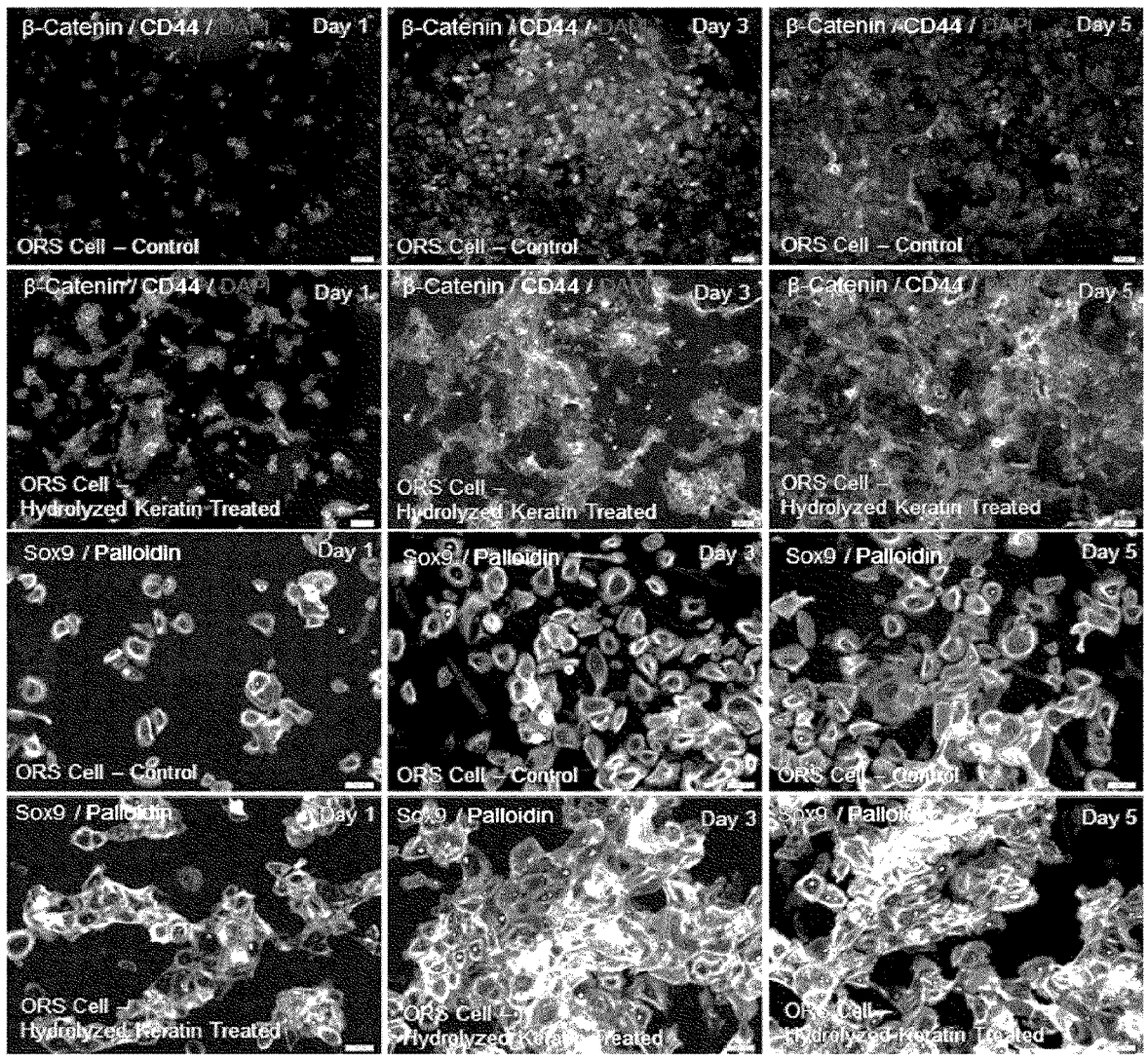
FIG. 13 is a diagram of confirming that expression of a beta-catenin molecule as a factor related with cell migration and activity of clone and a Sox-9 molecule involved in stemness is increased, when outer root sheath cells are treated with hydrolyzed keratin.

As a result, it was confirmed that in the case of human outer root sheath (ORS) cells, the expression of a beta-catenin molecule which is a factor related with migration of outer root sheath cells and activity of clone and a Sox-9 molecule involved in stemness was increased in relation with hair regeneration in the treatment of hydrolyzed keratin (FIG. 13). In addition, it was confirmed that the expression of a Sox-9 gene and a beta-catenin gene involved in stemness was increased (FIG. 14). In particular, it was confirmed that beta-catenin was expressed four times or more when treated with hydrolyzed keratin (FIG. 15).

Experimental Example 6: Expression Induction of Hair Growth-Related Factors of Hydrolyzed Keratin for Human Dermal Papilla Cells In Vitro Human dermal papilla (DP) cells were inoculated by $2 \times 10^5$ cells in a 6-well plate without any treatment. After 24 hours, the medium was replaced with a DP medium or a DP medium containing 1% (w/v) of hydrolyzed keratin. After 1, 2, and 3 days of incubation, the formation degree of cell aggregates and the activity degree of alkaline phosphatase were analyzed, and expression levels of beta-catenin, Sox-2, CD133, alkaline phosphatase, FGF7, and FGF10 were measured through immunohistochemical staining.

During the culturing of dermal papilla (DP) cells as described above, the number of cell aggregates produced during the treatment of hydrolyzed keratin was measured by an optical microscope.

In addition, after the culturing of dermal papilla (DP) cells as described above, the cells were immobilized by treating 4% paraformaldehyde for 1 to 2 minutes, washed with a rinse buffer contained in an alkaline phosphatase detection kit (Merk Millipore SCR004), added with 1 ml of a reaction solution in which Naphthol AS-BI phosphate solution: Fast Red Violet solution: distilled were mixed at 2:1:1, and then reacted at room temperature under a dark condition for 15 minutes. After the reaction, the cells stained by the activity of the alkaline phosphatase expressed by the alkaline phosphate cells were observed with a fluorescence microscope (Olympus Ix71).

After the human dermal papilla (DP) cells were cultured as described above, the medium was removed and the cells were washed with DPBS. The cells were immobilized by treating 4% paraformaldehyde for 10 minutes and then washed again with DPBS. After immobilization, 0.1% triton X-100 was treated for 30 minutes to be permeabilized and 10% (w/v) normal goat serum was treated for 1 hour. Thereafter, a rabbit anti-human beta-catenin antibody diluted at 1:200, a mouse anti-human Sox-2 antibody, a mouse anti-human ALPase antibody, a rabbit anti-human CD133 antibody, a mouse anti-human FGF-7 antibody, and a rabbit anti-human FGF-10 antibody were treated and reacted for 4° C. for 24 hours. After 24 hours of reaction, the cells were washed three times with DPBS, and a secondary Alexa Fluor 546 conjugated antibody and a secondary Alexa Fluor 488-conjugated antibody were treated at room temperature for 1 hour. Thereafter, the cells were washed three times with DPBS and treated with 4',6-diamidino-2-phenylindole (DAPI). The stained cells were observed with a fluorescence microscope (Olympus Ix71).

Figure 16:
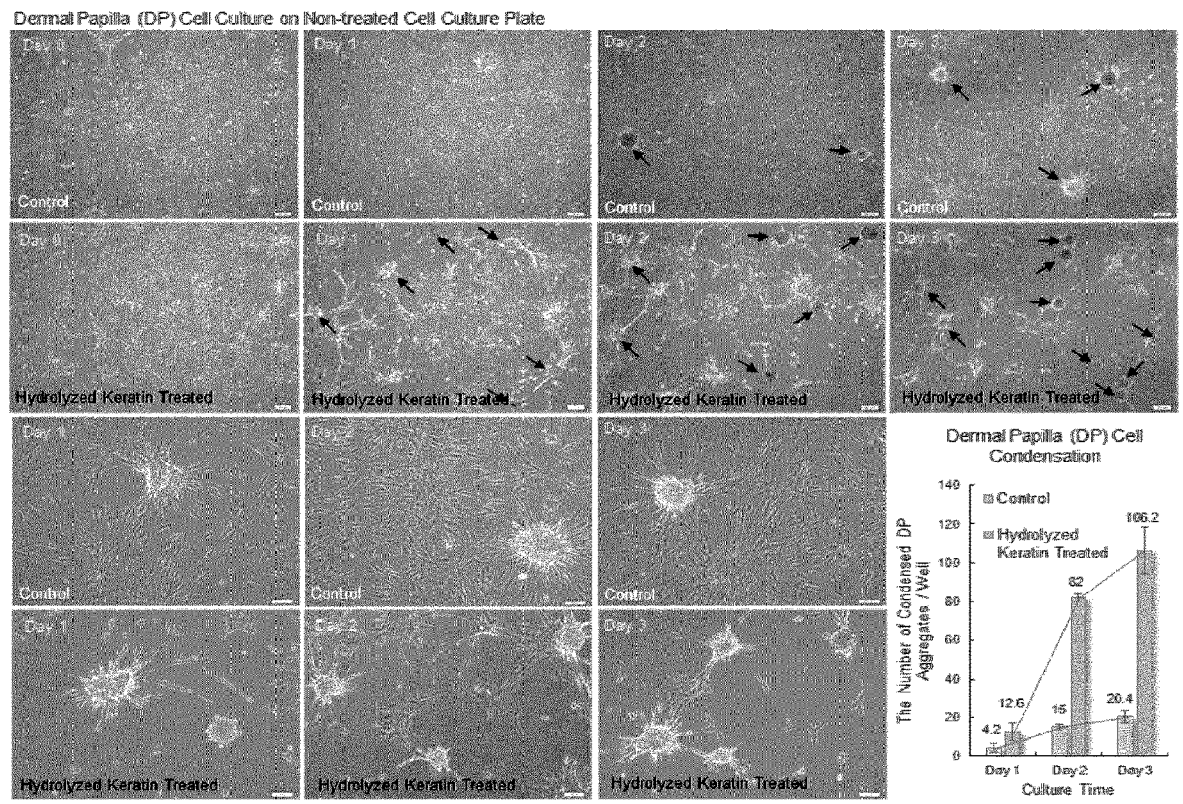
FIG. 16 is a diagram of confirming that formation of cell aggregates involved with hair regeneration and stemness is increased five times or more when human dermal papilla cells are treated with hydrolyzed keratin.
Figure 17:
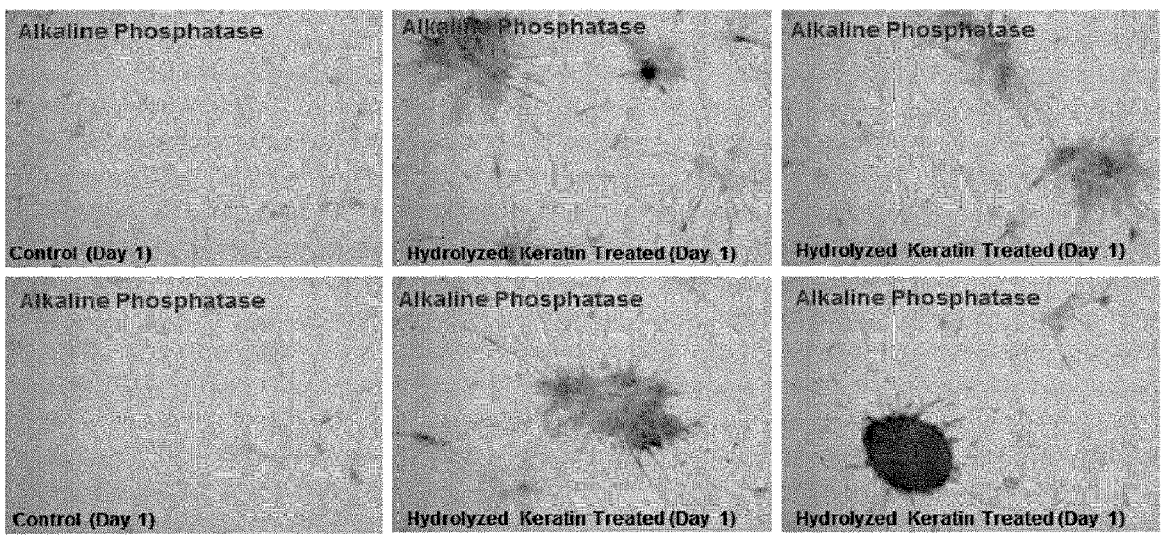
FIG. 17 is a photograph of confirming that activity of alkaline phosphatase by which alkaline phosphate cells are expressed is increased when human dermal papilla cells are treated with hydrolyzed keratin.
Figure 18:
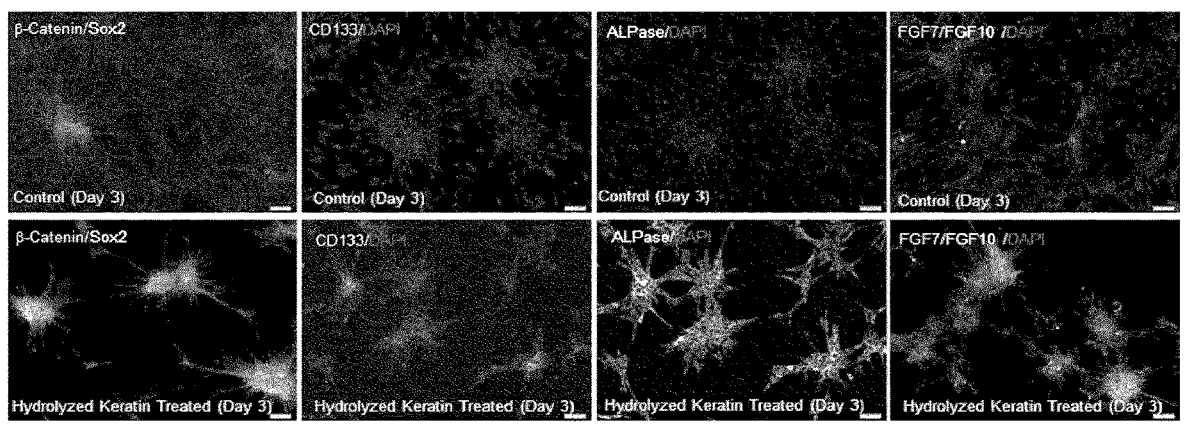
FIG. 18 is a photograph of confirming that expression of beta-catenin, Sox-2, alkaline phosphatase (ALPase), and CD133, FGF-7 and FGF-10 molecules as factors of hair regeneration and stemness is increased when human dermal papilla cells are treated with hydrolyzed keratin.

As a result, it was confirmed that in the case of dermal papilla (DP) cells, in the treatment of hydrolyzed keratin, the formation of cell aggregates involved in hair regeneration of dermal papilla cells and stemness was increased 5 times or more (FIG. 16), and the activity of the alkaline phosphatase expressed by alkaline phosphate cells was increased (FIG. 17). Furthermore, it was confirmed that the expression of beta-catenin, Sox-2, alkaline phosphatase, CD133, FGF-7, and FGF-10 molecules as factors for the hair regeneration of dermal papilla cells and stemness was increased (FIG. 18).

Through Experimental Examples 1 and 6, it was found that keratin increased the stemness of stem cells involved in hair regeneration and induced cell migration and differentiation to generate cell aggregates, thereby effectively inducing regeneration of hair.

The invention claimed is:

1. A method of stimulating hair growth, comprising the step of injecting a pharmaceutical composition containing keratin to a dermal layer or a subcutaneous tissue of a subject, wherein the keratin is in a concentration of 0.01 to 2 (w/v) %.

2. The method according to claim 1, wherein the keratin is hydrolyzed keratin or keratin linked to a water-soluble polymer.

3. The method according to claim 2, wherein the keratin is the hydrolyzed keratin and has a molecular weight of 500 to 10,000 Daltons.

4. The method according to claim 3, wherein the keratin is the keratin linked to a water-soluble polymer, and the water-soluble polymer is at least one selected from the group consisting of hyaluronic acid, polyethylene glycol (PEG), alginic acid, pectin, carrageenan, chondroitin sulfate, dextran sulfate, chitosan, polylysine, collagen, gelatin, carboxymethyl chitin, fibrin, dextran, agarose, pullulan, polyacrylamide (PAAm), poly(N-isopropylacrylamide) (P(NIPAAm-co-AAc)), poly(N-isopropylacrylamide-co-ethylmethacrylate) (P(NIPAAm-co-EMA)), polyvinyl acetate/polyvinyl alcohol (PVAc/PVA), poly(N-vinylpyrrolidone) (PVP), poly(methyl methacrylate-co-hydroxyethyl methacrylate) (P(MMA-co-HEMA)), poly(polyethyleneglycol-co-peptide) (P(PEG-co-peptide)), alginate-g-(polyethylene oxide-polypropylene oxide-polyethylene oxide)(alginate-g-(PEOPPO-PEO)), poly(polylactic acid-co-glycolic acid)-co-serine) (P(PLGA-co-serine)), collagenacrylate, alginate-acrylate, poly(hydroxypropyl methacrylamide-g-peptide) (P(HPMA-g-peptide)), poly(hydroxyethyl methacrylate/matrigel) (P(HEMA/Matrigel)), hyaluronic acid-g-N-isopropylacrylamide (HA-g-NIPAAm), polyethylene oxide (PEO), a polyethylene oxide-polypropylene oxide copolymer (PEO-PPO, Pluronic series), a polyethylene oxide-polylactic acid copolymer (PEO-PLA), a polyethylene oxide-polylactic glycolic acid copolymer (PEO-PLGA), a polyethylene oxide-polycaprolactone copolymer (PEO-PCL), polyoxyethylene alkyl ethers (Brij Series), polyoxyethylene castor oil derivatives (Cremophores), polyoxyethylene sorbitan fatty acid esters (Tween Series), and polyoxyethylene stearates.

5. The method according to claim 1, wherein the pharmaceutical composition increases an expression level of at least one selected from the group consisting of beta-catenin, SRY box transcription factor 9 (Sox-9), SRY box transcription factor 2 (Sox-2), alkaline phosphatase, prominin-1 (CD133), fibroblast growth factor 7 (FGF7), fibroblast growth factor 10 (FGF10), bone morphogenetic protein 6 (BMP6), P-cadherin, E-cadherin, msh homeobox 2 (MSX2), forkhead box N1 (FOXN1) and neprilysin (CD10).

6. The method according to claim 1, further comprising: a penetration enhancer.

7. The method according to claim 6, wherein the penetration enhancer is at least one selected from the group consisting of sulphoxide, azone, pyrrolidone, fatty acids, lower alcohols, higher fatty alcohols, glycols, urea, terpene, terpenoid, and phospholipid.

8. The method according to claim 2, wherein the keratin is the hydrolyzed keratin prepared by a preparation method of hydrolyzed keratin, including S1) reacting keratin with hydrolase; and S2) removing the hydrolase.

9. The method according to claim 8, wherein the hydrolase is at least one selected from the group consisting of Proteinase-K, Leucyl aminopeptidase, carboxypeptidase, pepsin, trypsin, and chymotrypsin.

10. The method according to claim 8, wherein the hydrolase is immobilized on beads.

11. The method according to claim 8, wherein the preparation method of hydrolyzed keratin further includes S3) removing the activity of the hydrolase after step S2) at a high temperature for several hours.

* * * * *